US010023581B2

(12) United States Patent
Callmann et al.

(10) Patent No.: US 10,023,581 B2
(45) Date of Patent: Jul. 17, 2018

(54) MODIFIED CYTOTOXINS AND THEIR THERAPEUTIC USE

(71) Applicants: The Regents of the University of California, Oakland, CA (US); Vybyl Holdings, Inc., Woodridge, IL (US)

(72) Inventors: Cassandra E. Callmann, San Diego, CA (US); Matthew P. Thompson, San Diego, CA (US); Nathan C. Gianneschi, San Diego, CA (US); Clare L. M. LeGuyader, San Diego, CA (US); Paul A. Bertin, Western Springs, IL (US)

(73) Assignees: The Regents of the University of California, Oakland, CA (US); Vybyl Holdings, Inc., Woodridge, IL (US)

( * ) Notice: Subject to any disclaimer, the term of this patent is extended or adjusted under 35 U.S.C. 154(b) by 0 days.

(21) Appl. No.: 15/271,822

(22) Filed: Sep. 21, 2016

(65) Prior Publication Data

US 2017/0080094 A1 Mar. 23, 2017

Related U.S. Application Data

(60) Provisional application No. 62/222,059, filed on Sep. 22, 2015.

(51) Int. Cl.

*C07D 475/08* (2006.01)
*C07D 305/14* (2006.01)
(Continued)

(52) U.S. Cl.

CPC ........ *C07D 491/044* (2013.01); *A61K 9/0019* (2013.01); *A61K 47/542* (2017.08);
(Continued)

(58) Field of Classification Search

CPC .............. C07D 491/044; C07D 305/14; C07D 475/08; C07D 491/22; A61K 47/542; A61K 9/0019; A61K 47/42; C07H 15/252
(Continued)

(56) References Cited

U.S. PATENT DOCUMENTS

| | | | | |
|---|---|---|---|---|
| 6,391,913 B1 * | 5/2002 | Page | C07D 305/14 | 514/449 |
| 2007/0141093 A1 * | 6/2007 | Zhang | A61K 31/337 | 424/400 |

(Continued)

FOREIGN PATENT DOCUMENTS

| | | |
|---|---|---|
| AU | 735205 | 11/1998 |
| KR | 10-1435261 | 9/2014 |

(Continued)

OTHER PUBLICATIONS

Goto; Chem Pharm Bull 1985, 33, 4422-4431.*

(Continued)

*Primary Examiner* — Daniel R Carcanague

(74) *Attorney, Agent, or Firm* — Kilpatrick Townsend & Stockton LLP

(57) ABSTRACT

The present disclosure generally provides compounds useful for treating cancer. In some aspects, the disclosure provides small-molecule cytotoxins that are chemically modified to include one or more moieties that include hydrophobic portions. In some embodiments, the disclosure provides small-molecule cytotoxins that are chemically modified with fatty acid-containing moieties. In some aspects, the disclosure provides compositions, such as pharmaceutical compositions, that include such modified small-molecule cytotoxins and a protein. In some embodiments, the protein is
(Continued)

albumin or an albumin mimetic. Further, the disclosure provides various uses of these compounds and compositions.

21 Claims, 2 Drawing Sheets

(51) Int. Cl.

| | |
|---|---|
| ***C07D 491/22*** | (2006.01) |
| ***A61K 31/427*** | (2006.01) |
| ***A61K 47/42*** | (2017.01) |
| ***A61K 31/337*** | (2006.01) |
| ***A61K 31/519*** | (2006.01) |
| ***A61K 31/704*** | (2006.01) |
| ***A61K 31/4745*** | (2006.01) |
| ***C07H 15/252*** | (2006.01) |
| ***C07D 491/044*** | (2006.01) |
| ***A61K 9/00*** | (2006.01) |
| ***A61K 47/54*** | (2017.01) |

(52) U.S. Cl.
CPC ......... *C07D 305/14* (2013.01); *C07D 475/08* (2013.01); *C07D 491/22* (2013.01); *C07H 15/252* (2013.01); *A61K 47/42* (2013.01)

(58) Field of Classification Search
USPC .......................................................... 549/200
See application file for complete search history.

(56) References Cited

U.S. PATENT DOCUMENTS

| | | | | |
|---|---|---|---|---|
| 2007/0203058 | A1 | 8/2007 | Lau et al. | |
| 2007/0259889 | A1 | 11/2007 | Klaveness et al. | |
| 2008/0103110 | A1 | 5/2008 | Klaveness et al. | |
| 2008/0207507 | A1 | 8/2008 | Lau et al. | |
| 2009/0275519 | A1 | 11/2009 | Nash et al. | |
| 2010/0240883 | A1 | 9/2010 | Wu et al. | |
| 2010/0286186 | A1 | 11/2010 | Franklin et al. | |
| 2012/0309944 | A1 | 12/2012 | Behrens et al. | |
| 2013/0012684 | A1 | 1/2013 | Buchardt | |
| 2013/0040883 | A1 | 2/2013 | Demuth et al. | |
| 2013/0053433 | A1 | 2/2013 | Cho et al. | |
| 2013/0267547 | A1 | 10/2013 | Gerk et al. | |
| 2013/0274182 | A1 | 10/2013 | Erickson et al. | |
| 2014/0107019 | A1 | 4/2014 | Erickson et al. | |
| 2014/0107324 | A1 | 4/2014 | Behrens et al. | |
| 2014/0235535 | A1 | 8/2014 | Erickson et al. | |
| 2014/0256621 | A1 | 9/2014 | Erickson et al. | |
| 2014/0364595 | A1 | 12/2014 | Bapat et al. | |
| 2016/0136190 | A1* | 5/2016 | Weichert .............. | A61K 31/337 514/100 |
| 2018/0000951 | A1* | 1/2018 | Callmann ............ | A61K 47/542 |

FOREIGN PATENT DOCUMENTS

| | | |
|---|---|---|
| WO | WO 2011/143201 | 11/2011 |
| WO | WO 2014201026 | * 12/2014 |

OTHER PUBLICATIONS

Siraki; Toxicological Sciences 2004, 81, 148-159.*
Ostergaard; Molecules 2007, 12, 2380-2395.*
Skwarczynski; J. Med. Chem. 2006, 49, 7253-7269.*
Food & Drug Administration, Briefing Document, NDA No. 21-660, Sep. 7, 2006.
Pharmacology/Toxicology Review, NDA No. 21-660, Dec. 2004.
Hoy et al., Drugs, vol. 74, pp. 1757-1768 (2014).
Reagan-Shaw et al., FASEB J., publ. online Oct. 17, 2007.
Neuzillet et al., Pharmacol Therapeutics, vol. 155, pp. 80-104 (2015).
Wunder et al., J. Immunol., vol. 170, pp. 4793-4801 (2003).
Thakor et al., Ca. Cancer J. Clin. vol. vol. 63, pp. 395-418 (2013).
Gurachevsky et al., Cancer Invest. , vol. 25, pp. 387-383 (2007).
Currie et al., Cell Metabol., vol. 18, Aug. 6, 2013.
Chan et al., Bioconjugate Chem., vol. 20, pp. 1194-1200 (2009).
Lou et al. J. Applied Polymer Sci., vol. 2014. pp. 1-7 (2014).
Dennis et al. J. Biol. Chem., vol. 277, pp. 35035-35043 (2002).
Bae et al. J. Controlled Release, vol. 153, pp. 198-205 (2011).
Kratz, "A Clinical Update of Using Albumin as a Drug Vehicle" (2014).
Bern et al., J. Controlled Relrease, vol. 211, pp. 144-162 (2015).
Kratz et al., J. Med. Chem., vol. 43, pp. 1253-1256 (2000).
Choi et al., J. Lipid Res., vol. 43, pp. 1000-1010 (2002).
Gibson et al., J. Am. Chem. Soc., vol. 129, pp. 11652-11661 (2007).
Chawla et al., J. Am. Med. Assoc. Oncology. pp. E1-E9 (2015).
Wolfrum et al., Nature Biotechnol., vol. 25, pp. 1149-1157 (2007).
Int'l Search Report & Written Opinion of the Int'l Searching Authority, PCT App. No. PCT/US2016/052829, dated Feb. 1, 2017.
Cline et al., Biomacromolecules, vol. 14, pp. 654-664 (2013).
Ducry, Antibody-Drug Conjugates (2013).
Ikuta et al., Chem. Commun., vol. 51, pp. 12835-12838 (2012).
Jain et al., Bioorg. Chem., vol. 49, pp. 40-48 (2013).
Li et al., Biomacomolecules, vol. 12, pp. 2016-2026 (2011).
Lodyato et al., Bioorg. Med. Chem. Lett., vol. 14, pp. 4253-4256 (2004).
Nissen et al., J. Med. Chem., vol. 58, pp. 1575-1580 (2015).
Rekowski et al., J. Med. Chem. vol. 56, pp. 8948-8952 (2013).
Santos et al., Bioorg. Med. Chem. vol. 15, pp. 1266-1274 (2007).
Schneider et al., Bioorg. Med. Chem., vol. 13, pp. 2799-2808 (2005).
Mueller et al., Nature Rev. Drug Discovery, vol. 11, pp. 751-761 (2012).
Von Hoff, New Eng. J. Med., vol. 369, pp. 1691-1701 (2013).
Engel et al., Expert Rev. Clin. Pharmacol., pp. 1-26 (2012).
Smith et al., Org. Biomol. Chem., vol. 13, pp. 7946-7949 (2015).
Neesse et al., Gut, pp. 1-10 (2013).
Wu et al., Proc. Nat'l. Acad. Sci., vol. 104, pp. 3990-3995 (2007).
Hayashi et al., Melanoma Res., pp. 1-10 (2010).
Wu et al., J. Innate Immunity, pp. 1-10 (2013).
Mahato et al., Adv. Drug Del. Rev., vol. 63, pp. 659-670 (2012).
Collery et al., Anticancer Res., vol. 32, pp. 2769-2782 (2012).
Basle et al., Chem. Biol. Rev., vol. 17, Mar. 26, 2010.
Stehle et al., Crit. Rev. Oncology Hematology, vol. 26, pp. 77-100 (1997).
Baenke et al., Disease Models & Mechanisms, vol. 6, pp. 1353-1363 (2013).
Kratz et al., "Serum Proteins as Drug Carriers of Anticancer Agents" in Drug Delivery in Oncology, pp. 747-803 (2012).
Van Der Vusse, Drug Metab. Pharmacokinet., vol. 24, pp. 300-307 (2009).
Sethi et al., Acta Poloniae Pharm. vol. 70, pp. 597-600 (2013).
Brodersen et al., Eu. J. Biochem. vol. 182, pp. 19-25 1989).
Sand et al., Frontiers in Immunology, vol. 5, pp. 1-21 (2015).
Yang et al., Int. J. Mol. Sci., vol. 15, pp. 3580-3595 (2014).
Shanmugam et al., Int. J. Pharmaceutics, vol. 403 pp. 130-135 (2011).
Awasthi et al., Carcinogenesis (2013) (advanced publication).
Bhattacharya et al., J. Mol. Biol., vol. 303, pp. 721-732 (2000).
Bhattacharyya et al., Nature Comm., (2015) (advanced publication).
Bradley et al., Clin. Cancer Res., vol. 7, pp. 3229,3238 (2001).
Burger et al., Int. J. Cancer, vol. 92, 718-724 (2001).
Curry et al., Nature Struct. Biol., vol. 5, pp. 827-835 (1998).
Deer et al., Pancreas, vol. 39, pp. 425-435 (2010).
Desai et al., Clin. Cancer Res., vol. 12, pp. 1317-1324 (2006).
Desai et al., Anti-Cancer Drugs, vol. 19, pp. 899-909 (2008).
Desai et al., Translational Oncology, vol. 2, pp. 59-64 (2009).
Elsadek et al., J. Controlled Release, vol. 157, pp. 4-28 (2012).
Feng et al., Cancer Chemother. Pharmacol. vol. 65, pp. 923-930 (2010).
Frei et al., Diebetology & Metabolic Syndrome (2011) (online publication).
Fu et al., Nature Sci. Reports (2015) (online publilcation).
Gardner et al., J. Chromatog. B, vol. 862, pp. 213-218 (2008).

(56) References Cited

OTHER PUBLICATIONS

Gilles et al., Cancer Res. vol. 58, pp. 5529-5536 (1998).
Gradishar, Exper Opin. Pharmacother, vol. 7, 1041-1053 (2006).
Hackett et al., J. Pharm. Sci., vol. 101, pp. 3292-3304 (2012).
Hawkins et al., Adv. Drug Del. Rev., vol. 60, pp. 876-885 (2008).
Iancu et al., Int. J. Nanomed., vol. 6, pp. 129-141 (2011).
Ibrahim et al., Clin. Cancer Res., vol. 8, pp. 1038-1044 (2002).
Jacobson et al., Bioconjugate Chem., vol. 27, p. 2239-2247 (Sep. 28, 2016).
Karmali et al., Nanomed., vol. 5, pp. 73-82 (2008).
Kim et al., Clin. Cancer Res., vol. 10, pp. 3708-3716 (2004).
Kratz et al., J. Controlled Release, vol. 161, pp. 429-445 (2012).
Kratz, J. Controlled Release, vol. 132, pp. 171-183 (2008).
Larsen et al., Molecular and Cellular Therapies (2016) (online publication).
Liebmann et al., Br. J. Cancer, vol. 69, pp. 1104-1109 (1993).
Lim et al., J. Controlled Release, vol. 170, pp. 219-225 (2013).
Merlot et al., Frontiers in Physiology, vol. 5, pp. 1-7 (2014).
Miele et al., Int. J. Nanomed., vol. 4, pp. 99-105 (2009).
Mocan et al., Int. J. Nanomed., vol. 10, pp. 5435-5445 (2015).
Neumann et al., Expert Opin. Drug Delivery, vol. 7, pp. 915-925 (2010).
Oida, J. Biochem., vol. 100, pp. 1533-1542 (1986).
Podhajcer et al., Cancer Metastasis Rev., vol. 27, pp. 691-705 (2008).
Ren et al., J. Nanomed. Nanotechnol., vol. 4 (2013) (online publication).
Sato et al., Oncogene, vol. 22, pp. 5021-5030 (2003).
Schnitzer et al. J. Biol. Chem., vol. 269, pp. 6072-6082 (1994).
Schnitzer, Am. J. Physiol., vol. 262, pp. H246-H254 (1992).
Spector, J. Lipid Res., vol. 16, pp. 165-179 (1975).
Sugio et al., Protein Engineering, vol. 12, pp. 439-446 (1999).
Surapaneni et al., ISRN Pharmacol., vol. 2012 (2012) (online publication).
Tai et al., Drug Resistance Updates, vol. 11, pp. 231-246 (2008).
Thomas et al., Clin. Cancer Res., vol. 6, pp. 1140-1149 (2000).
Tonsgard et al., J. Clin. Invest., vol. 82, pp. 1567-1573 (1988).
Trynda-Lemiesz, Bioorg. Med. Chem., vol. 12, pp. 3269-3275 (2004).
Van Der Vusse et al., Adv. Exp. Med. Biol., vol. 441, pp. 181-191 (1998).
Vanhoefer et al., Ann. Oncology, vol. 8, Pp. 1221-1228 (1997).
Zheng et al., J. Am. Chem. Soc., vol. 136, pp. 8790-8798 (2014).
Kang et al., Amino Acids, vol. 48, pp. 1667-1675 (Apr. 20, 2016).
Sella, Group Meeting Presentation (2013).
Unger et al., Cancer Therapy: Clinical, vol. 13, pp. 4858-4866 (2007).
Clegg, Am. J. Physiol., vol. 246, pp. R133-R151 (1984).
Kazantzis et al., Biochimica et Biophysica Acta, vol. 1821, pp. 852-857 (2012).
Sauer et al., Biochem. Society Trans., vol. 18, pp. 80-82 (1990).
Ke et al., Biomaterials, vol. 31, pp. 5855-5864 (2010).
Balaban et al., BioMed Res. Int'l., vol. 2015, pp. 1-17 (2015).
Tolle et al., BMC Cancer, vol. 11, pp. 1-10 (2011).
Kampan et al., BioMed Res. Int'l., vol. 2015, pp. 1-21 (2015).
Ward et al., Cancer Cell, vol. 21, pp. 297-308 (2012).
Kell et al., Nature Rev., Communication (2016).
Commisso et al., Nature, vol. 497, p. 633-637 (2013).
Fu et al., Nature: Scientific Reports, pp. 1-10 (2015).
Wu et al., Obstet. Gynecol. Int., vol. 1, pp. 1-7 (2014).
Glatz et al., Prostaglandins, Leukotrienes, and Essential Fatty Acids, vol. 92, pp. 57-62 (2015).
Dixon, Trends Endocrinol. Metab., vol. 21, pp. 480-487 (2010).
Bradley et al., Clin. Cancer Res., vol. 7, pp. 3229-3238 (2001).
Wolff et al., Clin. Cancer Res., vol. 9, pp. 3589-3597 (2003).
Sauer et al., Cancer Res., vol. 46 pp. 3469-3475 (1986).
Bos, Cancer Res., vol. 49, pp. 4682-4689 (1989).
Dong et al., Cancer Res., vol. 69, pp. 3918-3926 (2009).
Bracci et al., Cell Death Differentiation, vol. 21, pp. 15-25 (2014).
Deberardinis et al., Cell Metabol., vol. 7, pp. 11-19 (2008).
McKeague et al., Coord. Chem. Rev., vol. 232, pp. 127-135 (2002).
Sinha et al., Electrophoresis, vol. 20, pp. 2952-2960 (1999).
Huang et al., FEBS J., vol. 281, pp. 2266-2283 (2014).
Merlot et al., Frontiers in Physoil., vol. 5, pp. 1-7 (2014).
White, Genes & Devel., vol. 27, pp. 2065-2071 (2013).
Smathers et al., Human Genomics, vol. 5, pp. 170-191 (2011).
Schall et al., J. Autoimmunity, vol. 39, pp. 143-153 (2012).
Shin et al., J. Miomed. Mat. Res. A, vol. 102, pp. 575-587 (2014).
Chen et al., J. Clin. Pharmacol. vol. 54, pp. 1097-1107 (2014).
Skwarczynski et al., J. Med. Chem., vol. 49, pp. 7254-7269 (2006).
Ansell et al., J. Med. Chem., vol. 51, pp. 3288-3296 (2008).
Lau et al., J. Med. Chem., vol. 58, pp. 7370-7380 (2015).
Coe et al., J. Biol. Chem., vol. 274, pp. 36300-36304 (1999).
Larche et al., Nature Med., vol. 11, pp. S69-S76 (2005).
Altman et al., Nature Rev., pp. 1-16 (2016).

* cited by examiner

MODIFIED CYTOTOXINS AND THEIR THERAPEUTIC USE

CROSS-REFERENCE TO RELATED APPLICATIONS

The present application claims the benefit of priority of U.S. Provisional Application No. 62/222,059, filed Sep. 22, 2015, which is hereby incorporated by reference as though set forth herein in its entirety.

TECHNICAL FIELD

The present disclosure generally provides compounds useful for treating cancer. In some aspects, the disclosure provides small-molecule cytotoxins that are chemically modified to have one or more moieties that include hydrophobic portions. In some aspects, the disclosure provides compositions, that include such modified small-molecule cytotoxins and a protein, such as albumin or albumin mimetics. Further, the disclosure provides various uses of these compounds and compositions.

DESCRIPTION OF RELATED ART

Cancer refers to a group of diseases characterized by the formation of malignant tumors or neoplasms, which involve abnormal cell growth and have the potential to invade adjacent tissue and spread to other parts of the body. There are more than 14 million new diagnoses of cancer annually. Moreover, cancer accounts for more than 8 million deaths each year, which is about 15% of all deaths worldwide. In developed countries, cancer accounts for an even higher percentage of deaths.

Therapies for cancer have improved significantly over the years. In particular, an increasing number of cytotoxic agents have been discovered. These agents generally work by killing the cancer cells. But cytotoxic agents can be harmful to normal cells as well. Therefore, subjects undergoing treatment with such agents often suffer certain side-effects from the treatment. In some cases, the side-effects pose such a substantial risk that it may be necessary to administer very limited quantities of cytotoxic agents. So, while there is a general desire to discover increasingly toxic chemotherapeutic agents, it is also desirable to develop new means of directing those compounds selectively to cancer cells and away from normal cells.

Various strategies have been used to assist in directing chemotherapeutic agents selectively to cancer cells. For example, certain compounds rely on passive targeting, where the compound is selectively directed toward cancer cells (e.g., in a solid tumor) as a result of the fact that cancer cells tend to divide more rapidly than other cells and therefore have a higher appetite for certain biological building blocks. For example, gemcitabine, a commonly used cytotoxin, contains a sugar-like moiety as well as a toxic payload (a 5-fluorouracil moiety). Because cancer cells may have a higher need for sugar than other cells, gemcitabine is passively drawn to rapidly dividing cancer cells because it looks like a sugar molecule. Once at the cancer cell, gemcitabine can release its toxic payload. In some other cases, the targeting may be active, where the cytotoxic agent includes a moiety that binds selectively to a protein that is overexpressed in certain cancer cells. For example, pemetrexed includes a moiety that mimics folic acid, and thereby allows the drug to actively target cancer cells that overexpress folic acid receptors.

Such passive and active targeting has allowed for the development of increasingly toxic cytotoxic agents that have reduced side-effects with respect to earlier-generation cytotoxins. Even so, progress has been slow, and it is often impractical to build certain features into cytotoxic agents that allow them to target cancer cells selectively and also be formulated in a way that is suitable for delivery. Therefore, there is a continuing need to discover new ways of selectively directing cytotoxic agents to cancer cells.

SUMMARY

The present disclosure provides compounds and compositions that can deliver increasingly toxic quantities of a cytotoxin to cancer cells (e.g., in a solid tumor) with reduced side-effects with respect to other non-cancerous cells. In some embodiments, the compounds are prodrugs of small-molecule cytotoxins, such that the prodrug permits improved delivery of the cytotoxin to a solid tumor in a mammal. The disclosure also provides methods and uses of those compounds and compositions for the treatment of cancer.

In a first aspect, the disclosure provides compounds of formula (I):

$$A^1\text{-}X^1\text{—}X^2\text{-}A^2 \quad \text{(I)}$$

wherein: $A^1$ is an organic group, or is a hydrophilic group of a hydrogen atom; $A^2$ is a cytotoxic drug moiety, which has a molecular weight of no more than 1600 Da; $X^1$ is a hydrophobic group; and $X^2$ is a direct bond, an organic group, or a heteroatom group selected from the group consisting of —O—, —S—, —S(═O)—, —S(═O)$_2$—, —S—S—, —N═, ═N—, —N(H)—, —N═N—N(H)—, —N(H)—N═N—, —N(OH)—, or —N(═O)—. In some embodiments, $A^1$ is a hydrophilic group, such as a carboxylic acid group (—COOH) or pharmaceutically acceptable salts thereof. In some embodiments, the cytotoxic drug moiety is a paclitaxel moiety, a doxorubicin moiety, or a pemetrexed moiety. In some embodiments, the hydrophobic group is a $C_{12-22}$ hydrocarbylene group, which is optionally substituted. In some embodiments, $X^2$ is an organic group, such as a carbonyl group, i.e., —C(═O)—.

In a second aspect, the disclosure provides a compound of the following formula:

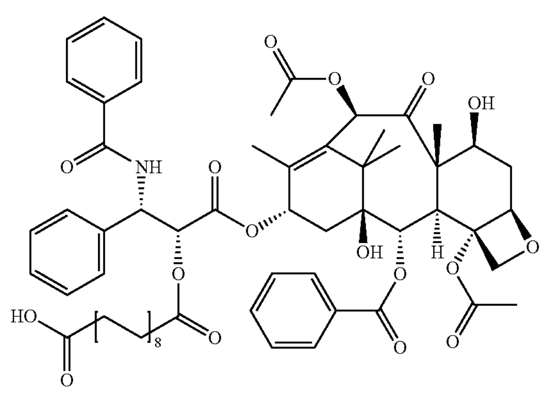

or a pharmaceutically acceptable salt thereof.

In a third aspect, the disclosure provides compositions (e.g., pharmaceutical compositions) that include: a compound of any embodiments of the foregoing aspects; and a protein. In some embodiments, the protein is an albumin or an albumin mimetic.

In a fourth aspect, the disclosure provides compositions (e.g., pharmaceutical compositions) that include: a compound of any embodiments of the first or second aspects; a protein, wherein the protein is an albumin or an albumin mimetic; and a carrier, which includes water; wherein the compound and the protein are non-covalently associated with each other; and wherein the compound and the protein are solvated by the carrier.

In a fifth aspect, the disclosure provides methods of treating cancer, which include administering to a subject a compound or composition of any embodiments of any of the foregoing aspects.

In a sixth aspect, the disclosure provides methods of inducing apoptosis in a cancer cell, which include contacting the cancer cell with a compound or composition of any embodiments of any of the first through the fourth aspects.

In a seventh aspect, the disclosure provides methods for inhibiting growth of a cancerous tumor, which includes contacting the cancerous tumor with a compound of any embodiments of the first or second aspects.

In an eighth aspect, the disclosure provides uses of a compound or composition of any embodiments of any of the first through the fourth aspects as a medicament.

In a ninth aspect, the disclosure provides uses of a compound or composition of any embodiments of any of the first through the fourth aspects for treating cancer.

In a tenth aspect, the disclosure provides uses of a compound or composition of any embodiments of any of the first through the fourth aspects in the manufacture of a medicament.

In an eleventh aspect, the disclosure provides uses of a compound or composition of any embodiments of any of the first through the fourth aspects in the manufacture of a medicament for treating cancer.

In a twelfth aspect, the disclosure provides methods of making compounds of the first and second aspects and compositions of the third and fourth aspects.

Further aspects and embodiments are provided in the drawings, the detailed description, the claims, and the abstract.

BRIEF DESCRIPTION OF DRAWINGS

The following drawings are provided for purposes of illustrating various embodiments of the compounds, compositions, methods, and uses disclosed herein. The drawings are provided for illustrative purposes only, and are not intended to describe any preferred compounds or compositions or any preferred methods or uses, or to serve as a source of any limitations on the scope of the claimed inventions.

DETAILED DESCRIPTION

Figure 1:
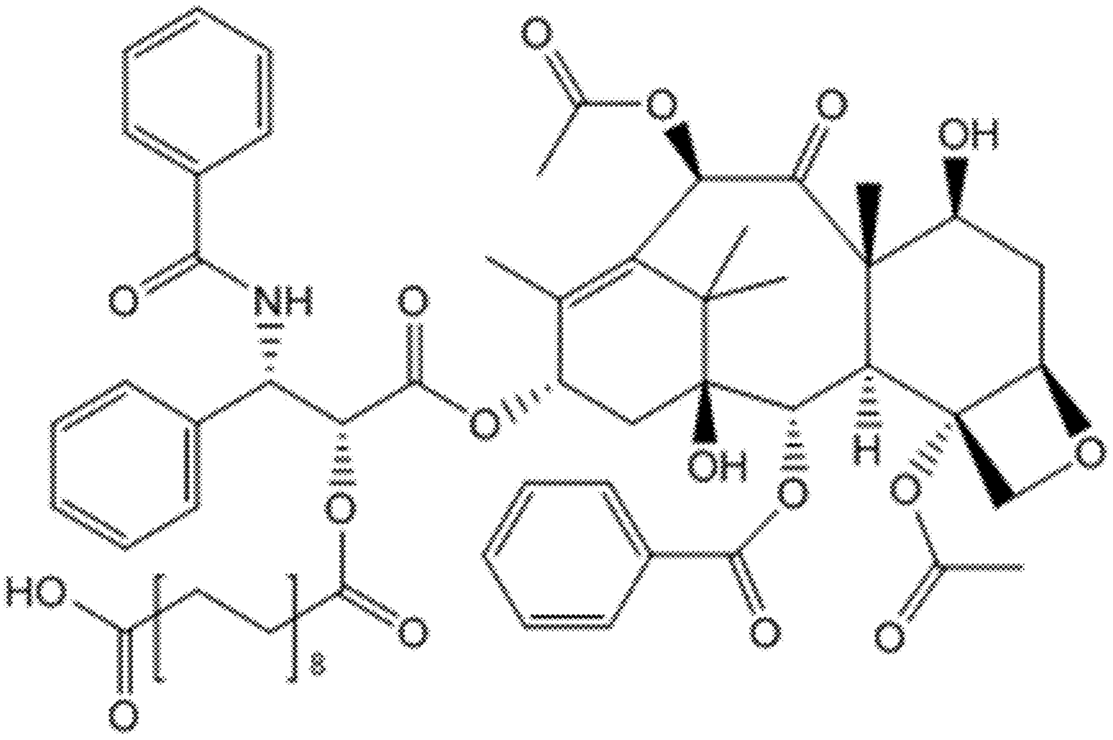
FIG. 1 shows a non-limiting example of a compound of formula (I), where the compound is paclitaxel, which is modified to include an ester of octadecanedioic acid.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "hydrocarbon" refers to an organic group composed of carbon and hydrogen, which can be saturated or unsaturated, and can include aromatic groups. The term "hydrocarbyl" refers to a monovalent or polyvalent (e.g., divalent or higher) hydrocarbon moiety. In some cases, a divalent hydrocarbyl group is referred to as a "hydrocarbylene" group.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. In some instances, the "alkyl" group can be divalent, in which case, the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, sulfur dioxides, and carbonyl groups, where feasible), and is referred to as a "heteroalkyl" or "heteroalkylene" group, respectively. Non-limiting examples include "oxyalkyl" or "oxyalkylene" groups, which refer to groups where a carbon atom in the alkyl or alkylene group is replaced by oxygen. Non-limiting examples of oxyalkyl or oxyalkylene groups include alkyl or alkylene chains that contain a carbonyl group, and also alkoxylates, polyalkylene oxides, and the like.

The number of carbon atoms in any group or compound can be represented by the terms. Thus, "$C_z$" refers to a group of compound having z carbon atoms, and "$C_{x-y}$", refers to a group or compound containing from x to y, inclusive, carbon atoms. For example, "$C_{1-6}$ alkyl" represents an alkyl group having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. The same logic applies to other types of functional groups, defined below.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the carbon atoms in the alkenyl or alkenylene group can be replaced by a heteroatom (e.g., selected from nitrogen, oxygen, or sulfur, including N-oxides, sulfur oxides, sulfur dioxides, and carbonyl groups, where feasible), and is referred to as a "heteroalkenyl" or "heteroalkenylene" group, respectively.

As used herein, "cycloalkyl" refers to an aliphatic saturated or unsaturated hydrocarbon ring system having 3 to 20 carbon atoms, which may be optionally substituted, as herein further described, with multiple degrees of substitution being allowed. In some embodiments, the term refers only to saturated hydrocarbon ring systems, substituted as herein further described. Examples of "cycloalkyl," as used herein, include, but are not limited to, cyclopropyl, cyclobutyl, cyclopentyl, cyclohexyl, cyclohexenyl, cycloheptyl, cyclooctyl, adamantyl, and the like. In some instances, the "cycloalkyl" group can be divalent, in which case the group can alternatively be referred to as a "cycloalkylene" group. Cycloalkyl and cycloalkylene groups can also be referred to herein as "carbocyclic rings." Also, in some instances, one or more of the carbon atoms in the cycloalkyl or cycloalkylene group can be replaced by a heteroatom (e.g., selected independently from nitrogen, oxygen, silicon, or sulfur, including N-oxides, sulfur oxides, and sulfur dioxides, where feasible), and is referred to as a "heterocyclyl" or "heterocyclylene" group, respectively. The term "heterocyclic ring" can also be used interchangeably with either of these terms. In some embodiments, the cycloalkyl and heterocyclyl groups are fully saturated. In some other embodiments, the cycloalkyl and heterocyclyl groups can contain one or more carbon-carbon double bonds.

As used herein, "halogen," "halogen atom," or "halo" refer to a fluorine, chlorine, bromine, or iodine atom. In some embodiments, the terms refer to a fluorine or chlorine atom.

As used herein, the terms "organic group," "organic moiety," or "organic residue" refer to a monovalent or polyvalent functional group having at least one carbon atom, which optionally contains one or more additional atoms selected from the group consisting of hydrogen atoms, halogen atoms, nitrogen atoms, oxygen atoms, phosphorus atoms, and sulfur atoms, and which does not include covalently bound metal or semi-metal atoms. In some embodiments, these terms can include metal salts of organic groups, such as alkali metal or alkaline earth metal salts of organic anions.

As used herein, the term "pharmacophore" refers to a type of organic functional group. Standard pharmacophores are hydrophobic pharmacophores, hydrogen-bond donating pharmacophores, hydrogen-bond accepting pharmacophores, positive ionizable pharmacophores, and negative ionizable pharmacophores. The classification of organic functional groups within a compound is carried out according to standard classification systems known in the art.

As used herein, the terms "hydrophobic group," "hydrophobic moiety," or "hydrophobic residue" refer to an organic group that consists essentially of hydrophobic pharmacophores. In some embodiments, the terms refer to an organic group that consists of hydrophobic pharmacophores.

As used herein, the terms "hydrophilic group," "hydrophilic moiety," or "hydrophilic residue" refer to an organic group that comprises one pharmacophores selected from the group consisting of hydrogen bond donors, hydrogen bond acceptors, negative ionizable groups, or positive ionizable groups. In some embodiments, the terms refer to an organic group that consist essentially of pharmacophores selected from the group consisting of hydrogen bond donors, hydrogen bond acceptors, negative ionizable groups, or positive ionizable groups.

As used herein, the term "drug moiety" refers to a drug compound, or a pharmaceutically acceptable salt thereof, where an atom or a group of atoms is absent, thereby creating a monovalent or polyvalent moiety. In some embodiments, for example, a hydrogen atom is absent, thereby creating a monovalent moiety. In some other embodiments, a functional group, such as an —OH moiety, an —$NH_2$ moiety, or a —COOH, moiety is absent. In some embodiments, the drug moiety is a "cytotoxic drug moiety," which refers to a drug moiety (as defined above) of a cytotoxic drug compound. One non-limiting example of such a "drug moiety," (in this case, a "paclitaxel moiety") is the moiety of the following formula:

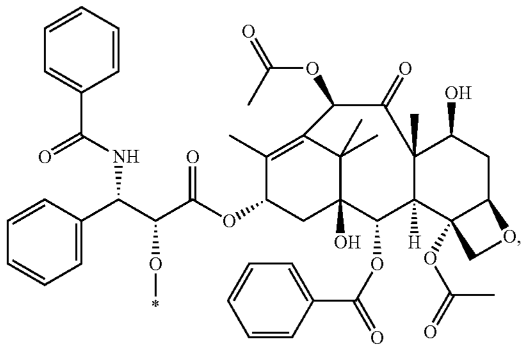 [SMILES: *O[C@@H](C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](OC(C)=O)C(=C1C)C2(C)C)[C@@H](NC(=O)c1ccccc1)c1ccccc1]

where a hydrogen atom is absent to create a monovalent moiety that, within a compound, bonds to the rest of the molecule through the remaining oxygen atom. Note that the term "drug moiety" is not limited to any particular procedure for making such compounds.

Various methods of drawing chemical structures are used herein. In some instances, the bond line-structure method is used to depict chemical compounds or moieties. In the line-structure method, the lines represent chemical bonds, and the carbon atoms are not explicitly shown (but are implied by the intersection of the lines). The hydrogen atoms are also not explicitly shown, except in instances where they are attached to heteroatoms. Heteroatoms, however, are explicitly shown. Thus, using that methodology, the structures shown below are for 2-methylpropane, 1-methoxypropane, and 1-propanol:

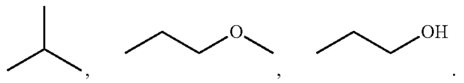

In that methodology, aromatic rings are typically represented merely by one of the contributing resonance structures. Thus, the following structures are for benzene, pyridine, and pyrrole:

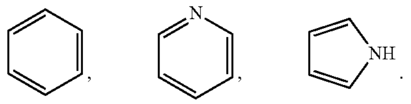 [SMILES: c1ccccc1 ; c1ccncc1 ; c1cc[nH]c1]

As used herein, a "protein binding moiety" is a moiety that binds non-covalently to one or more sites on a protein with a binding constant ($K_b$) of at least 100 $M^{-1}$ in water at 25° C.

As used herein, "amino acid" refers to a compound having the structure $H_2N—R^x—COOH$, where $R^x$ is an organic group, and where the $NH_2$ may optionally combine with Rx (e.g., as in the case of proline). The term includes any known amino acids, including, but not limited to, alpha amino acids, beta amino acids, gamma amino acids, delta amino acids, and the like. In some embodiments, the term can refer to alpha amino acids.

As used herein, "hydroxy acid" refers to a compound having the structure $HO—R^y—COOH$, where $R^y$ is an organic group. Non-limiting examples include glycolic acid, lactic acid, and caprolactone.

As used herein, "alkanol amine" refers to a compound having the structure $HO—R^z—NH_2$, where $R^z$ is an optionally substituted alkylene group. Non-limiting examples include ethanol amine.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of: delaying the progress of a disease, disorder, or condition; controlling a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In some embodiments, the "subject" is a human. In some such embodiments, the "subject" is a human who exhibits one or more symptoms characteristic of a disease, disorder, or condition. The term "subject" does not require one to have any particular status with respect to a hospital, clinic, or research facility (e.g., as an admitted patient, a study participant, or the like).

As used herein, the term "compound" includes free acids, free bases, and salts thereof.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

Also included within the scope of the disclosure are the individual enantiomers of the compounds represented by Formula (I) or pharmaceutically acceptable salts thereof, as well as any wholly or partially racemic mixtures thereof. The disclosure also covers the individual enantiomers of the compounds represented by Formula (I) or pharmaceutically acceptable salts thereof, as well as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure, except for the replacement of a hydrogen atom by a deuterium or tritium, or the replacement of a carbon atom by a $^{13}C$- or $^{14}C$-enriched carbon are within the scope of the disclosure.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present. As used herein, the phrases "consist essentially of," "consists essentially of," and "consisting essentially of" refer to groups that are open, but which only includes additional unnamed members that would not materially affect the basic characteristics of the claimed subject matter.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (—) or a dash used in combination with an asterisk (*). In other words, in the case of $—CH_2CH_2CH_3$ or $*—CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Modified Cytotoxins

In at least one aspect, the disclosure provides compounds of formula (I):

$$A^1\text{-}X^1—X^2\text{-}A^2 \quad (I)$$

wherein: $A^1$ is a hydrophilic group or a hydrogen atom, or is an organic group; $A^2$ is a cytotoxic drug moiety; $X^1$ is a hydrophobic group; and $X^2$ is a direct bond, an organic group, or a group selected from the group consisting of —O—, —S—, —S(═O)—, $—S(═O)_2—$, —S—S—, —N═, ═N—, —N(H)—, —N═N—N(H)—, —N(H)—N═N—, —N(OH)—, or —N(═O)—.

In some embodiments, $A^1$ is an organic group. $A^1$ can contain any suitable number of carbon atoms. In some embodiments, for example, $A^1$ contains from 1 to 100 carbon atoms, or from 1 to 50 carbon atoms, or from 1 to 25 carbon atoms, or from 1 to 10 carbon atoms, or from 1 to 6 carbon atoms. $A^1$ can also contain one or more heteroatoms, such as nitrogen, oxygen, sulfur, or phosphorus.

In some embodiments according to any of the foregoing embodiments, $A^1$ is a hydrophilic group or moiety. Non-limiting examples of a hydrophilic group include, but are not limited to, a carboxylic acid moiety, an ester moiety, an amide moiety, a urea moiety, an amine moiety, an ether moiety, an alcohol moiety, a thioether moiety, a thiol moiety, a ketone moiety, an aldehyde moiety, a sulfate moiety, a thiosulfate moiety, a sulfite moiety, a thiosulfite moiety, a phosphate moiety, a phosphonate moiety, a phosphinate moiety, a phosphite moiety, a borate moiety, or a boronate moiety.

In some embodiments of any of the aforementioned embodiments, $A^1$ is selected from the group consisting of a carboxylic acid group (—COOH), a carboxylate anion ($—COO^-$), or a carboxylate ester ($—COOR^a$, where $R^a$ is an organic group such as an alkyl or alkoxylate group). In some such embodiments, $A^1$ is a carboxylic acid group. In some such embodiments, $A^1$ is a carboxylate ester group.

In some other embodiments of any of the aforementioned embodiments, $A^1$ is a hydrogen atom. In some other embodiments of any of the aforementioned embodiments, $A^1$ is a hydroxyl (—OH) group.

In any of the aforementioned embodiments, $X^1$ can be a hydrophobic group having any suitable number of carbon atoms. In some embodiments, for example, $X^1$ contains from 1 to 100 carbon atoms, or from 1 to 50 carbon atoms, or from 1 to 25 carbon atoms.

In some embodiments of any of the aforementioned embodiments, $X^1$ is $C_{8-30}$ hydrocarbylene, which is optionally substituted. In some further embodiments, $X^1$ is $C_{12-22}$ hydrocarbylene, which is optionally substituted. In some further embodiments, $X^1$ is $C_{12-22}$ alkylene. In some further embodiments, $X^1$ is $—(CH_2)_{12}—$, $—(CH_2)_{14}—$, $—(CH_2)_{16}—$, $—(CH_2)_{18}—$, $—(CH_2)_{20}—$, or $—(CH_2)_{22}—$. In some other embodiments, $X^1$ is $—(CH_2)_{16}—$. In some further embodiments, $X^1$ is $C_{12-22}$ alkenylene. In some further such embodiments, $X^1$ is $—(CH_2)_7—CH═CH—(CH_2)_7—$.

In some embodiments of any of the aforementioned embodiments, $X^2$ is a direct bond. In some other embodiments of any of the aforementioned embodiments, $X^2$ is an organic group. In some embodiments, $X^2$ is a hydrophilic group. In some embodiments, $X^2$ is a heteroalkylene group.

In any of the aforementioned embodiments where $X^2$ is an organic group, $X^2$ can contain any suitable number of carbon atoms. In some embodiments, for example, $X^2$ contains from 1 to 100 carbon atoms, or from 1 to 50 carbon atoms, or from 1 to 25 carbon atoms, or from 1 to 10 carbon atoms, or from 1 to 6 carbon atoms.

In any of the aforementioned embodiments where $X^2$ is a heteroalkylene group, $X^2$ can contain any suitable number of carbon atoms. In some embodiments, for example, $X^2$ contains from 1 to 100 carbon atoms, or from 1 to 50 carbon atoms, or from 1 to 25 carbon atoms, or from 1 to 10 carbon atoms, or from 1 to 6 carbon atoms.

In some of the aforementioned embodiments, $X^2$ can contain certain groups. Some non-limiting examples of such groups that $X^2$ can contain are polyalkylene oxide groups, such as polyethylene glycol (PEG) and various polypeptide chains.

In some embodiments, $X^2$ is an organic group selected from the group consisting of —C(═O)—, —C≡C—, —C(H)═C(H)—, —C(═O)—O—, —O—C(═O)—, —C(═O)—NH—, —NH—C(═O)—, —NH—C(═O)—O—, —O—(C═O)—NH—, —O—C(═O)—O—, $—C(═N—NH_2)—$, $—C(═N—R^b)—$ (where $R^b$ is a hydrogen atom or an alkyl group), —C(═N—OH)—, —NH—C(═O)—NH—, —NH—C(═S)—NH—, —NH—C(═S)—O—, —O—C(═S)—NH—, —NH—C(═O)—S—, —S—C(═O)—NH—,—NH—C(═S)—S—, —S—C(═S)—NH—, and the cyclic structures shown below:

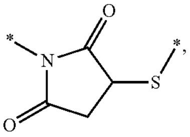, 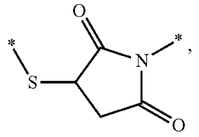, 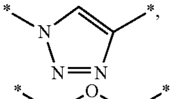, 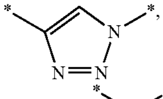, 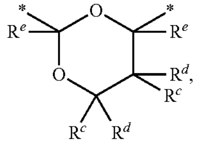 and 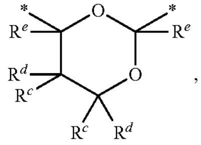, where $R^c$, $R^d$, and $R^e$ are, independently at each occurrence, a hydrogen atom or $C_{1-10}$ alkyl. In some further embodiments, $X^2$ is —C(═O)—.

In some embodiments, $X^2$ is a group selected from the group consisting of —O—, —S—, —S(═O)—, —S (=O)$_2$—, —S—S—, —N=, =N—, —N(H)—, —N=N—N(H)—, —N(H)—N=N—, —N(OH)—, and —N(O)—.

In some embodiments, $X^2$ comprises one or more moieties selected from the group consisting of: —C(=O)—, —O—C(=O)—, —NH—C(=O)—, one or more moieties formed from a alkylene glycols, one or more units formed from alkanol amines, one or more units formed from amino acids, and one or more units formed from hydroxyl acids. Thus, in some embodiments, $X^2$ comprises one or more moieties formed from alkylene glycols, such as a short poly(ethylene glycol) chain having 1 to 25 ethylene glycol units. In some embodiments, $X^2$ comprises one or more moieties formed from amino acids, such as an oligopeptide chain having 1 to 25 amino acid units. In some embodiments, $X^2$ comprises one or more moieties formed from hydroxy acids, such as moieties formed from glycolic acid, lactic acid, or caprolactone. In some embodiments, $X^2$ comprises a combination of a poly(ethylene glycol) chain having 1 to 25 ethylene glycol units and an oligopeptide having 1 to 25 amino acid units, and optionally one or more units formed from hydroxy acids.

In any of the above embodiments, the selection of $X^2$ will depend on the type of functional group through which it is linked to the cytotoxic drug moiety, so as to avoid making compounds that are chemically unstable or impossible. The skilled artisan will be able to select combinations of $X^2$ and $A^2$ that result in chemically stable compounds, which are compounds in which the chemical structure is not substantially altered when kept at a temperature from about −80° C. to about +40° C., in the absence of moisture or other chemically reactive conditions, for at least a week.

In the above embodiments, $A^2$ can be any suitable cytotoxic drug moiety. In some embodiments, the cytotoxic drug moiety is a small-molecule drug moiety, such as a cytotoxic drug moiety having a molecular weight of or no more than 1600 Da, or no more than 1500 Da, or no more than 1400 Da, or no more than 1300 Da, no more than 1200 Da, or no more than 1100 Da, or no more than 1000 Da, or no more than 900 Da. Such drug moieties can be organic moieties, or can also be moieties that contain inorganic atoms (e.g., platinum). In some embodiments, however, the cytotoxic drug moiety is an organic moiety.

In some embodiments of any of the aforementioned embodiments, the cytotoxic drug moiety is a moiety selected from the group consisting of: a paclitaxel moiety, an etoposide moiety, a gemcitabine moiety, a cyclophosphamide moiety, a chlorambucil moiety, a doxorubicin moiety, a daunorubicin moiety, a 5-fluorouracil moiety, a dactinomycin moiety, an amifostine moiety, a fludarabine moiety, a topotecan moiety, an ifosfamide moiety, a vincristine moiety, a carboplatin moiety, a vinblastine moiety, an imatinib moiety, a lenalidomide moiety, a pemetrexed moiety, an abiraterone moiety, an erlotinib moiety, a bortezomib moiety, an oxaliplatin moiety, a methotrexate moiety, a carfilzomib moiety, a crizotinib moiety, a vismodegib moiety, a ponatinib moiety, a tivozanib moiety, a carbozantinib moiety, an epirubicin moiety, a docetaxel moiety, a cisplatin moiety, an eribulun moiety, an ixabepilone moiety, a vinorelbine moiety, an everolimus moiety, a mytomycin C moiety, a sunitinib moiety, an irinotecan moiety, a leicovorim moiety, a tretinoin moiety, an allopurinol moiety, an asparaginase moiety, a bendamustine moiety, a bleomycin moiety, a folinic acid moiety, a capecitabine moiety, a cytarabine moiety, a dacarbazine moiety, a filgrastim moiety, a hydroxycarbamide moiety, a mercaptopurine moiety, a mesna moiety, a procarbazine moiety, a thioguanine moiety, and pharmaceutically acceptable salts of any of the foregoing. In some further such embodiments, the cytotoxic drug moiety is a moiety selected from the group consisting of: a paclitaxel moiety, an etoposide moiety, a gemcitabine moiety, a cyclophosphamide moiety, a chlorambucil moiety, a doxorubicin moiety, a daunorubicin moiety, a 5-fluorouracil moiety, a dactinomycin moiety, an amifostine moiety, a fludarabine moiety, a topotecan moiety, an ifosfamide moiety, a vincristine moiety, a vinblastine moiety, an imatinib moiety, a lenalidomide moiety, a pemetrexed moiety, an abiraterone moiety, an erlotinib moiety, a bortezomib moiety, a methotrexate moiety, a carfilzomib moiety, a crizotinib moiety, a vismodegib moiety, a ponatinib moiety, a tivozanib moiety, a carbozantinib moiety, an epirubicin moiety, a docetaxel moiety, an eribulun moiety, an ixabepilone moiety, a vinorelbine moiety, an everolimus moiety, a mytomycin C moiety, a sunitinib moiety, an irinotecan moiety, a leicovorim moiety, and pharmaceutically acceptable salts of any of the foregoing. In some further such embodiments, the cytotoxic drug moiety is selected from the group consisting of: a paclitaxel moiety, a gemcitabine moiety, a doxorubicin moiety, a 5-fluorouracil moiety, a methotrexate moiety, and a pemetrexed moiety. In some further such embodiments, the cytotoxic drug moiety is a paclitaxel moiety. In some further such embodiments, the cytotoxic drug moiety is a gemcitabine moiety. In some further such embodiments, the cytotoxic drug moiety is a 5-fluorouracil moiety. In some further such embodiments, the cytotoxic drug moiety is a pemetrexed moiety.

In the aforementioned embodiments, the named moieties can have any suitable chemical form. In some embodiments of any of the aforementioned embodiments, the cytotoxic drug moieties are moieties where a hydrogen atom is absent from the named drug compound, or a pharmaceutically acceptable salt thereof. As a non-limiting example, such a "paclitaxel moiety" would include the moiety of the following formula:

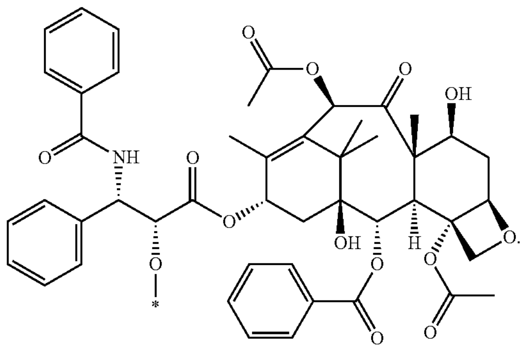 [SMILES: *O[C@@H](C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](OC(C)=O)C(=C1C)C2(C)C)[C@@H](NC(=O)c1ccccc1)c1ccccc1]

In some instances, racemization may occur at the point of attachment of the moiety. Thus, another non-limiting example would include the moiety of the following formula:

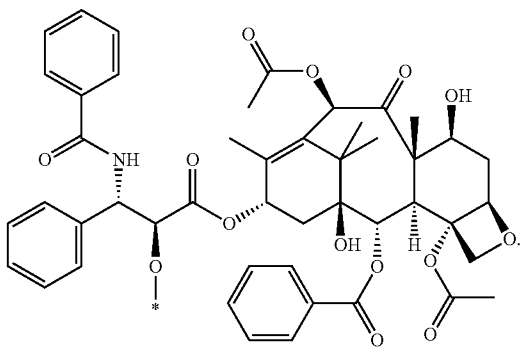

The structures below show various non-limiting examples of compounds that are included within the scope of compounds of formula (I), as defined above. Note that, at each occurrence, G is independently a hydrogen atom or —$X^2$—$X^1$-$A^1$ (according to any of the aforementioned embodiments), wherein, for each compound, at least one G is not a hydrogen atom. In some embodiments, for each compound, exactly one G is —$X^2$—$X^1$-$A^1$ (according to any of the aforementioned embodiments).

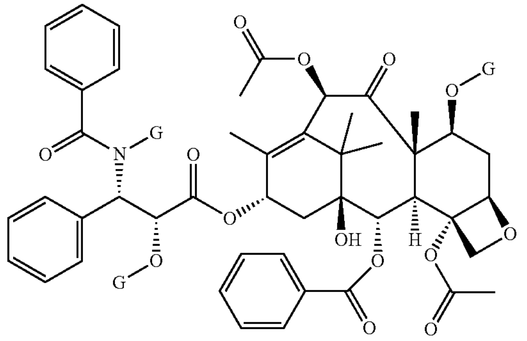

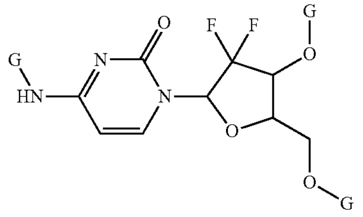

In the above structures, when G is —$X^2$—$X^1$-$A^1$ it can be —$X^2$—$X^1$-$A^1$ according to any of the previously recited embodiments, so long as those combinations result in stable chemical structures that would be suitable for pharmaceutical use. In some such embodiments, however, —$X^2$—$X^1$-$A^1$ is —C(═O)—$(CH_2)_{10}$—$CH_3$, —C(═O)—$(CH_2)_{12}$—$CH_3$, —C(═O)—$(CH_2)_{14}$—$CH_3$, or —C(═O)—$(CH_2)_{16}$—$CH_3$. In some other such embodiments, —$X^2$—$X^1$-$A^1$ is —C(═O)—$(CH_2)_{10}$—C(═O)—OH, —C(═O)—$(CH_2)_{12}$—C(═O)—OH, —C(═O)—$(CH_2)_{14}$—C(═O)—OH, or —C(═O)—$(CH_2)_{16}$—C(═O)—OH.

The selection of —$X^2$—$X^1$-$A^1$ can depend on the nature of the connection to the drug moiety.

For example, in embodiments where the —$X^2$—$X^1$-$A^1$ connects to an oxygen atom or an NH group on the drug moiety, as is the case for entries HA1, HA2, HA9, HA12, HA14, HA15, HA16, HA19, HA20, HA21, HA22, HA23, and HA24 in Table 1, then —$X^2$—$X^1$-$A^1$ is selected from the group consisting of: —C(═O)—$(CH_2)_{n1}$—C(═O)—OH; —C(═O)—$(CH_2)_{n1}$—C(═O)—$OCH_3$; —C(═O)—$(CH_2)_{n1}$—$CH_3$; —C(═O)—($C_{1-6}$ alkylene)-C(═O)—O—$(CH_2)_{n2}$—C(═O)—OH; —C(═O)—($C_{1-6}$ alkylene)-NH—C(═O)—$(CH_2)_{n1}$—C(═O)—OH; —C(═O)—($C_{1-6}$ alkylene)-C(═O)—O—$[(CH_2)_2$—O—$]_{n3}(CH_2)_{n2}$—C(═O)—OH; —C(═O)—O—$(CH_2)_{n2}$—C(═O)—OH; and —C(═O)—NH—$(CH_2)_{n2}$—C(═O)—OH; wherein n1 is an integer 12 to 24, n2 is an integer from 13 to 25, and n3 is an integer from 1 to 25. In some further such embodiments, —$X^2$—$X^1$-$A^1$ is selected from the group consisting of: —C(═O)—$(CH_2)_{n1}$—C(═O)—OH; —C(═O)—$(CH_2)_{n1}$—C(═O)—$OCH_3$; —C(═O)—($C_{1-6}$ alkylene)-C(═O)—O—$(CH_2)_{n2}$—C(═O)—OH; —C(═O)—($C_{1-6}$ alkylene)-NH—C(═O)—$(CH_2)_{n1}$—C(═O)—OH; —C(═O)—($C_{1-6}$ alkylene)-C(═O)—O—$[(CH_2)_2$—O—$]_{n3}(CH_2)_{n2}$—C(═O)—OH; —C(═O)—O—$(CH_2)_{n2}$—C(═O)—OH; and —C(═O)—NH—$(CH_2)_{n2}$—C(═O)—OH. In some further such embodiments, —$X^2$—$X^1$-$A^1$ is selected from the group consisting of: —C(═O)—$(CH_2)_{n1}$—C(═O)—OH; —C(═O)—O—$(CH_2)_{n2}$—C(═O)—OH; and —C(═O)—NH—$(CH_2)_{n2}$—C(═O)—OH. In some other embodiments, —$X^2$—$X^1$-$A^1$ is —C(═O)—($C_{1-6}$alkylene)-O—C(═O)—$(CH_2)_{n1}$—C(═O)—OH, where n1 is an integer from 12 to 24. In some embodiments of any of the aforementioned embodiments, n1 is an integer from 14 to 22, or from 16 to 20. In some embodiments of any of the aforementioned embodiments, n2 is an integer from 15 to 23, or from 17 to 21. In some embodiments of any of the aforementioned embodiments, n3 is an integer from 1 to 15, or from 1 to 10, or from 1 to 6. In some such embodiments, —$X^2$—$X^1$-$A^1$ is —C(═O)—($C_{1-6}$ alkylene)-C(═O)—O—$(CH_2)_{n3}$—OH, where n3 is an integer from 14 to 26, or an integer from 16 to 24, or an integer from 18 to 22.

In embodiments where the —$X^2$—$X^1$-$A^1$ connects to an >N group on the drug moiety, as is the case for entries HA3 and HA4 in Table 1, then —$X^2$—$X^1$-$A^1$ is selected from the group consisting of: —$CH_2$—O—C(═O)—$(CH_2)_{n1}$—C(═O)—OH; —$CH_2$—O—C(═O)—$(CH_2)_{n1}$—C(═O)—$OCH_3$; —$CH_2$—O—C(═O)—$(CH_2)_{n1}$—$CH_3$; —$CH_2$—O—C(═O)—($C_{1-6}$ alkylene)-C(═O)—O—$(CH_2)_{n2}$—C(═O)—OH; —$CH_2$—O—C(═O)—($C_{1-6}$ alkylene)-NH—C(═O)—$(CH_2)_{n1}$—C(═O)—OH; —$CH_2$—O—C(═O)—($C_{1-6}$ alkylene)-C(═O)—O—$[(CH_2)_2$—O—$]_{n3}(CH_2)_{n2}$—C(═O)—OH; —$CH_2$—O—C(═O)—O—$(CH_2)_{n2}$—C(═O)—OH; and —$CH_2$—O—C(═O)—NH—$(CH_2)_{n2}$—C(═O)—OH; wherein n1 is an integer 12 to 24, n2 is an integer from 13 to 25, and n3 is an integer from 1 to 25. In some further such embodiments, —$X^2$—$X^1$-$A^1$ is selected from the group consisting of: —$CH_2$—O—C(═O)—$(CH_2)_{n1}$—C(═O)—OH; —$CH_2$—O—C(═O)—$(CH_2)_{n1}$—C(═O)—$OCH_3$; —$CH_2$—O—C(═O)—($C_{1-6}$ alkylene)-C(═O)—O—$(CH_2)_{n2}$—C(═O)—OH; —$CH_2$—O—C(═O)—($C_{1-6}$ alkylene)-NH—C(═O)—$(CH_2)_{n1}$—C(═O)—OH; —$CH_2$—O—C(═O)—($C_{1-6}$ alkylene)-C(═O)—O—$[(CH_2)_2$—O—$]_{n3}(CH_2)_{n2}$—C(═O)—OH; —$CH_2$—O—C(═O)—O—$(CH_2)_{n2}$—C(═O)—OH; and —C(═O)—NH—$(CH_2)_{n2}$—C(═O)—OH. In some further such embodiments, —$X^2$—$X^1$-$A^1$ is selected from the group consisting of: —$CH_2$—O—C(═O)—$(CH_2)_{n1}$—C(═O)—OH; —$CH_2$—O—C(═O)—O—$(CH_2)_{n2}$—C(═O)—OH; and —$CH_2$—O—C(═O)—NH—$(CH_2)_{n2}$—C(═O)—OH. In some embodiments of any of the aforementioned embodiments, n1 is an integer from 14 to 22, or from 16 to 20. In some embodiments of any of the aforementioned embodiments, n2 is an integer from 15 to 23, or from 17 to 21. In some embodiments of any of the aforementioned embodiments, n3 is an integer from 1 to 15, or from 1 to 10, or from 1 to 6. In some such embodiments, —$X^2$—$X^1$-$A^1$ is —$CH_2$—O—C(═O)—($C_{1-6}$ alkylene)-C(═O)—O—$(CH_2)_{n3}$—OH, where n3 is an integer from 14 to 26, or an integer from 16 to 24, or an integer from 18 to 22.

In embodiments where the —$X^2$—$X^1$-$A^1$ connects to a —C(═O) group on the drug moiety, as is the case for entries HA5, HA6, HA7, HA8, HA11, and HA17 in Table 1, then —$X^2$—$X^1$-$A^1$ is selected from the group consisting of:

—O—$(CH_2)_{n2}$—C(═O)—OH; —NH—$(CH_2)_{n2}$—C(═O)—OH; —NH—($C_{1-6}$ alkylene)-O—C(═O)—$(CH_2)_{n1}$—C(═O)—OH; —O—($C_{1-6}$ alkylene)-O—C(═O)—$(CH_2)_{n1}$—C(═O)—OH; —NH—($C_{1-6}$ alkylene)-O—C(═O)—$(CH_2)_{n1}$—C(═O)—$OCH_3$; —O—($C_{1-6}$ alkylene)-O—C(═O)—$(CH_2)_{n1}$—C(═O)—$OCH_3$; —NH—($C_{1-6}$ alkylene)-O—C(═O)—$(CH_2)_{n1}$—$CH_3$; —O—($C_{1-6}$ alkylene)-O—C(═O)—$(CH_2)_{n1}$—$CH_3$; —NH—($C_{1-6}$ alkylene)-C(═O)—O—$[(CH_2)_2$—O—$]_{n3}(CH_2)_{n2}$—C(═O)—OH; and —O—($C_{1-6}$ alkylene)-C(═O)—O—$[(CH_2)_2$—O—$]_{n3}(CH_2)_{n2}$—C(═O)—OH; wherein n1 is an integer 12 to 24, n2 is an integer from 13 to 25, and n3 is an integer from 1 to 25. In some further such embodiments, —$X^2$—$X^1$-$A^1$ is selected from the group consisting of: —O—$(CH_2)_{n2}$—C(═O)—OH; —NH—$(CH_2)_{n2}$—C(═O)—OH; —NH—($C_{1-6}$ alkylene)-O—C(═O)—$(CH_2)_{n1}$—C(═O)—OH; —O—($C_{1-6}$ alkylene)-O—C(═O)—$(CH_2)_{n1}$—C(═O)—OH; —NH—($C_{1-6}$alkylene)-O—C(═O)—$(CH_2)_{n1}$—C(═O)—$OCH_3$; and —O—($C_{1-6}$ alkylene)-O—C(═O)—$(CH_2)_{n1}$—C(═O)—$OCH_3$. In some further such embodiments, —$X^2$—$X^1$-$A^1$ is selected from the group consisting of: —O—$(CH_2)_{n2}$—C(═O)—OH; —NH—$(CH_2)_{n2}$—C(═O)—OH; —NH—($C_{1-6}$ alkylene)-O—C(═O)—$(CH_2)_{n1}$—C(═O)—OH; and —O—($C_{1-6}$ alkylene)-O—C(═O)—$(CH_2)_{n1}$—C(═O)—OH. In some embodiments of any of the aforementioned embodiments, n1 is an integer from 14 to 22, or from 16 to 20. In some embodiments of any of the aforementioned embodiments, n2 is an integer from 15 to 23, or from 17 to 21. In some embodiments of any of the aforementioned embodiments, n3 is an integer from 1 to 15, or from 1 to 10, or from 1 to 6. In some such embodiments, —$X^2$—$X^1$-$A^1$ is —O—$(CH_2)_{n3}$—OH, where n3 is an integer from 14 to 26, or an integer from 16 to 24, or an integer from 18 to 22.

In embodiments where the —$X^2$—$X^1$-$A^1$ connects to a C═* group on the drug moiety, as is the case for entries HA10, HA13, and HA18 in Table 1, then —$X^2$—$X^1$-$A^1$ is selected from the group consisting of: ═N—O—$(CH_2)_{n2}$—C(═O)—OH; ═N—NH—$(CH_2)_{n2}$—C(═O)—OH; ═N—O—$(CH_2)_{n2}$—C(═O)—$OCH_3$; ═N—NH—$(CH_2)_{n2}$—C(═O)—$OCH_3$; ═N—O—$(CH_2)_{n2}$—$CH_3$; ═N—NH—$(CH_2)_{n2}$—$CH_3$; ═N—O—$[(CH_2)_2$—O—$]_{n3}(CH_2)_{n2}$—C(═O)—OH; and ═N—NH—$[(CH_2)_2$—O—$]_{n3}(CH_2)_{n2}$—C(═O)—OH; n2 is an integer from 13 to 25, and n3 is an integer from 1 to 25. In some further such embodiments, —$X^2$—$X^1$-$A^1$ is selected from the group consisting of: ═N—O—$(CH_2)_{n2}$—C(═O)—OH; ═N—NH—$(CH_2)_{n2}$—C(═O)—OH; ═N—O—$(CH_2)_{n2}$—C(═O)—$OCH_3$; and ═N—NH—$(CH_2)_{n2}$—C(═O)—$OCH_3$. In some further such embodiments, —$X^2$—$X^1$-$A^1$ is selected from the group consisting of: ═N—O—$(CH_2)_{n2}$—C(═O)—OH and ═N—NH—$(CH_2)_{n2}$—C(═O)—OH. In some embodiments of any of the aforementioned embodiments, n2 is an integer from 15 to 23, or from 17 to 21. In some embodiments of any of the aforementioned embodiments, n3 is an integer from 1 to 15, or from 1 to 10, or from 1 to 6. In some such embodiments, —$X^2$—$X^1$-$A^1$ is selected from the group consisting of: ═N—O—$(CH_2)_{n3}$—OH and ═N—NH—$(CH_2)_{n3}$—OH, where n3 is an integer from 14 to 26, or an integer from 16 to 24, or an integer from 18 to 22.

The compounds described in any of the above embodiments can also exist as pharmaceutically acceptable salts. The term "pharmaceutically acceptable salts" refers to salts of the compounds which are not biologically or otherwise undesirable and are generally prepared by reacting the free base with a suitable organic or inorganic acid or by reacting the acid with a suitable organic or inorganic base. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium, and valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, there can be formed an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate, and the like.

The compounds above can be made by standard organic synthetic methods, such as those illustrated in: Wuts et al., *Greene's Protective Groups in Organic Synthesis* (4th ed., 2006); Larock, *Comprehensive Organic Transformations* (2nd ed., 1999); and Smith et al., *March's Advanced Organic Chemistry: Reactions, Mechanisms, and Structure* (6th ed., 2007). Specific non-limiting examples are shown below in the Examples.

The compounds of the foregoing embodiments, including their pharmaceutically acceptable salts, are useful as cytotoxic agents or prodrugs thereof, and are therefore useful as compounds for the treatment of cancer.

Table 3 (below) shows various examples of compounds that are contemplated by the present disclosure. Table 3 refers to various combinations of an $A^2$- moiety with a —$X^2$—$X^1$-$A^1$, which together form compounds of the present disclosure. Table 1 shows illustrative example moieties for the $A^2$- moiety, wherein $A^2$ can be the moiety shown or can also be a pharmaceutically acceptable salt thereof. Table 2 shows illustrative example moieties for —$X^2$—$X^1$-$A^1$. Table 3 shows non-limiting illustrative combinations of the moieties from Tables 1 and 2, which can come together to form compounds of the present disclosure. The compounds disclosed in Table 3 can be made by methods analogous to those illustrated in the Examples, and by common synthetic methods known to those of ordinary skill in the art. Suitable methods of making such compounds are illustrated in: Wuts et al., *Greene's Protective Groups in Organic Synthesis* (4th ed., 2006); Larock, *Comprehensive Organic Transformations* (2nd ed., 1999); and Smith et al., *March's Advanced Organic Chemistry: Reactions, Mechanisms, and Structure* (6th ed., 2007).

TABLE 1
| $A^2$-Moieties | |
|---|---|
| HA1 | 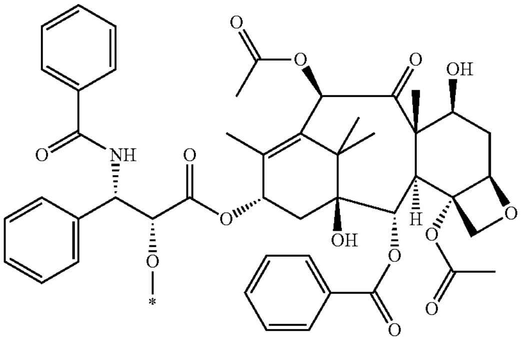 [SMILES: *O[C@@H](C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](OC(C)=O)C(=C1C)C2(C)C)[C@@H](NC(=O)c1ccccc1)c1ccccc1]<br>a paclitaxel moiety |
| HA2 | 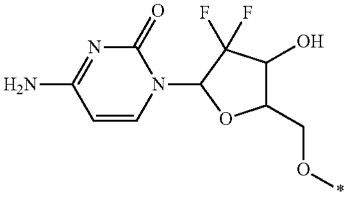 [SMILES: *OCC1OC(n2ccc(N)nc2=O)C(F)(F)C1O]<br>a gemcitabine moiety |
| HA3 | 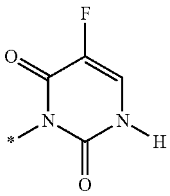 [SMILES: *n1c(=O)[nH]cc(F)c1=O]<br>a 5-fluorouracil moiety |
| HA4 | 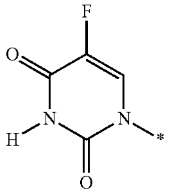 [SMILES: *n1cc(F)c(=O)[nH]c1=O]<br>a 5-fluorouracil moiety |
| HA5 | 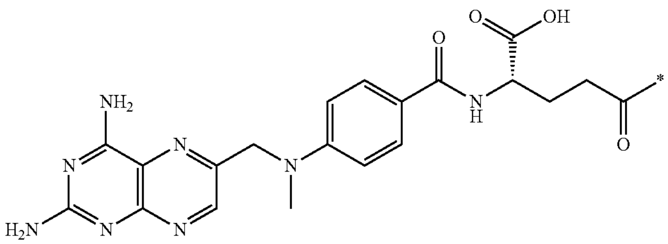 [SMILES: *C(=O)CC[C@H](NC(=O)c1ccc(N(C)Cc2cnc3nc(N)nc(N)c3n2)cc1)C(=O)O]<br>a methotrexate moiety |

TABLE 1-continued
| A²-Moieties |
| --- |
HA6
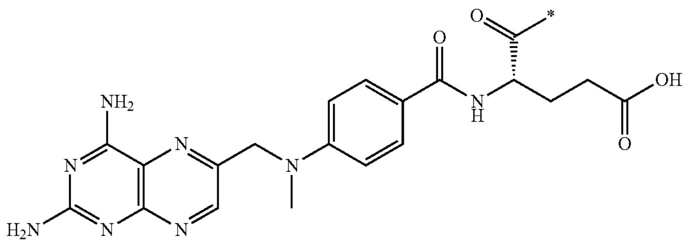 [SMILES: *C(=O)[C@H](CCC(=O)O)NC(=O)c1ccc(N(C)Cc2cnc3nc(N)nc(N)c3n2)cc1]
a methotrexate moiety
HA7
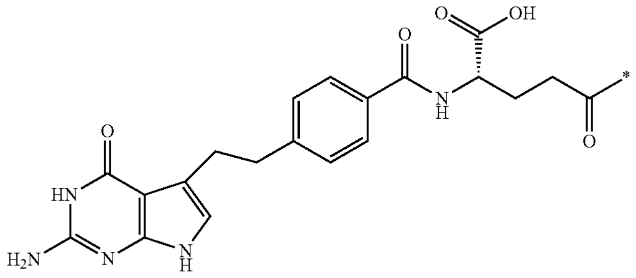 [SMILES: *C(=O)CC[C@H](NC(=O)c1ccc(CCc2c[nH]c3nc(N)[nH]c(=O)c23)cc1)C(=O)O]
a pemetrexted moiety
HA8
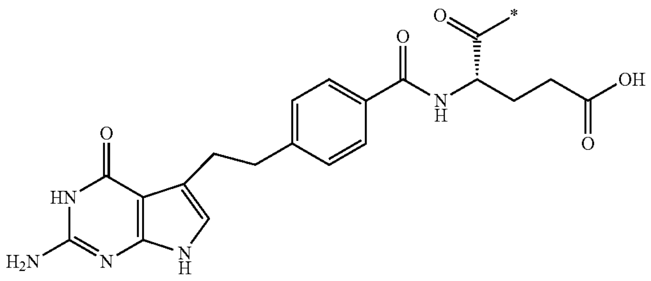 [SMILES: *C(=O)[C@H](CCC(=O)O)NC(=O)c1ccc(CCc2c[nH]c3nc(N)[nH]c(=O)c23)cc1]
a pemetrexted moiety
HA9
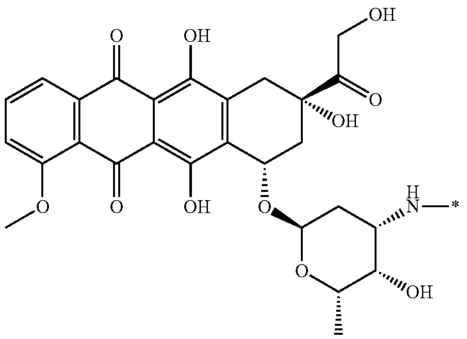 [SMILES: *N[C@H]1C[C@H](O[C@H]2C[C@](O)(C(=O)CO)Cc3c(O)c4c(c(O)c32)C(=O)c2c(OC)cccc2C4=O)O[C@@H](C)[C@H]1O]
a doxorubicin moiety TABLE 1-continued
| A$^2$-Moieties | |
|---|---|
| HA10 | 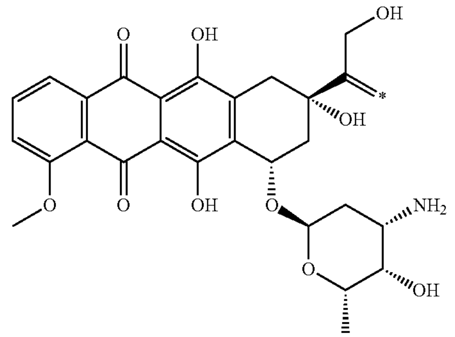 [SMILES: *=C(CO)[C@]1(O)Cc2c(O)c3c(c(O)c2[C@@H](O[C@H]2C[C@H](N)[C@H](O)[C@H](C)O2)C1)C(=O)c1c(OC)cccc1C3=O] a doxorubicin moiety |
| HA11 | 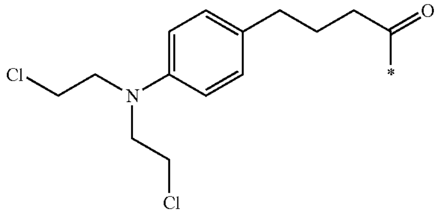 [SMILES: *C(=O)CCCc1ccc(N(CCCl)CCCl)cc1] a chlorambucil moiety |
| HA12 | 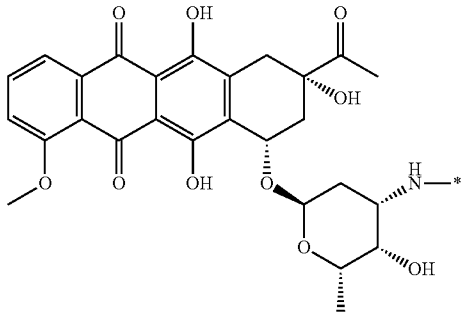 [SMILES: *N[C@H]1C[C@H](O[C@H]2C[C@](O)(C(C)=O)Cc3c(O)c4c(c(O)c32)C(=O)c2c(OC)cccc2C4=O)O[C@@H](C)[C@H]1O] a daunorubicin moiety |
| HA13 | 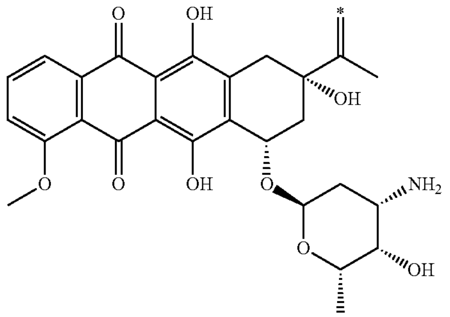 [SMILES: *=C(C)[C@]1(O)Cc2c(O)c3c(c(O)c2[C@@H](O[C@H]2C[C@H](N)[C@H](O)[C@H](C)O2)C1)C(=O)c1c(OC)cccc1C3=O] a daunorubicin moiety |

TABLE 1-continued
| A²-Moieties | |
|---|---|
| HA14 | 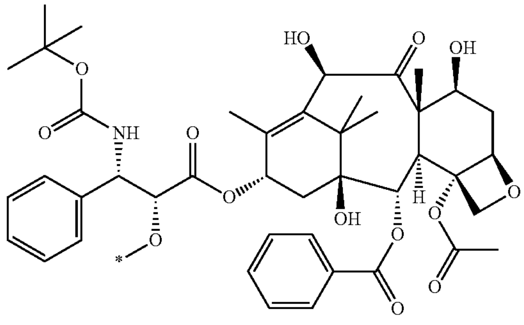 [SMILES: *O[C@@H](C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](O)C(=C1C)C2(C)C)[C@@H](NC(=O)OC(C)(C)C)c1ccccc1]<br>a docetaxel moiety |
| HA15 | 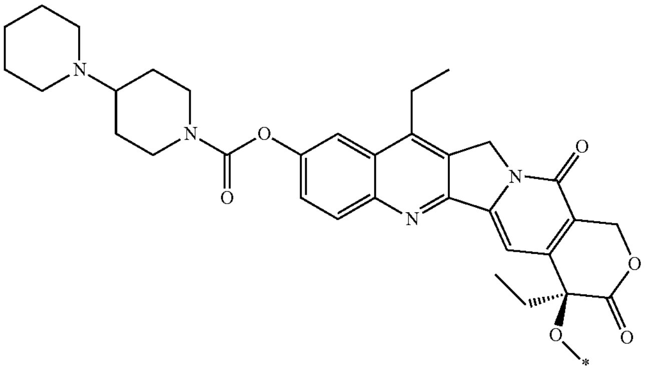 [SMILES: *O[C@]1(CC)C(=O)OCc2c1cc1n(c2=O)Cc2c-1nc1ccc(OC(=O)N3CCC(N4CCCCC4)CC3)cc1c2CC]<br>an irinotecan moiety |
| HA16 | 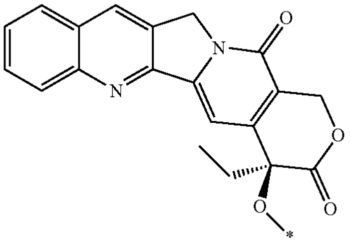 [SMILES: *O[C@]1(CC)C(=O)OCc2c1cc1n(c2=O)Cc2cc3ccccc3nc2-1]<br>a camptothecin moiety |
| HA17 | 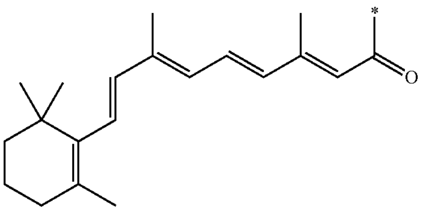 [SMILES: *C(=O)/C=C(C)/C=C/C=C(C)/C=C/C1=C(C)CCCC1(C)C]<br>a tertinoin moiety |

TABLE 1-continued
| A²-Moieties | |
|---|---|
| HA18 | 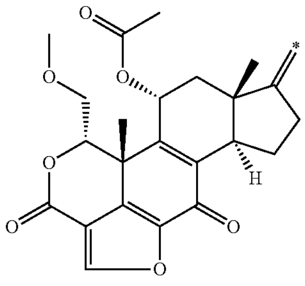 [SMILES: *=C1CC[C@H]2C3=C([C@H](OC(C)=O)C[C@]12C)[C@]1(C)c2c(coc2C3=O)C(=O)O[C@@H]1COC]<br>a wortmannin moiety |
| HA19 | 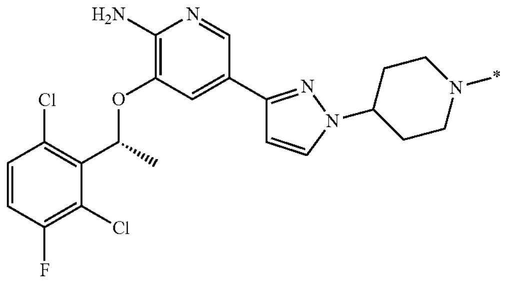 [SMILES: *N1CCC(n2ccc(-c3cnc(N)c(O[C@H](C)c4c(Cl)ccc(F)c4Cl)c3)n2)CC1]<br>a crizotinib moiety |
| HA20 | 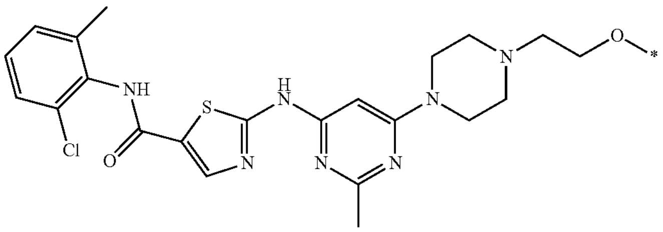 [SMILES: *OCCN1CCN(c2cc(Nc3ncc(C(=O)Nc4c(C)cccc4Cl)s3)nc(C)n2)CC1]<br>a dasatinib moiety |
| HA21 | 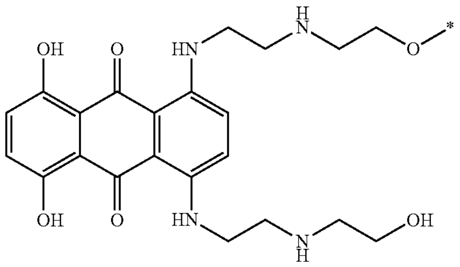 [SMILES: *OCCNCCNc1ccc(NCCNCCO)c2c1C(=O)c1c(O)ccc(O)c1C2=O]<br>a mitoxantrone moiety |
| HA22 | 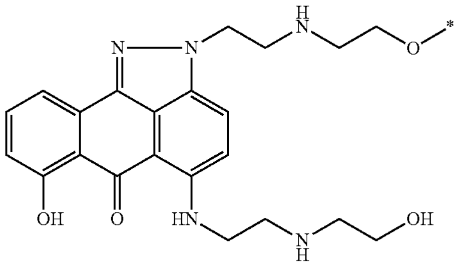 [SMILES: *OCCNCCn1nc2c3c(c(NCCNCCO)ccc31)C(=O)c1c(O)cccc1-2]<br>a losaxantrone moiety |

TABLE 1-continued

| | $A^2$-Moieties |
|---|---|
| HA23 | 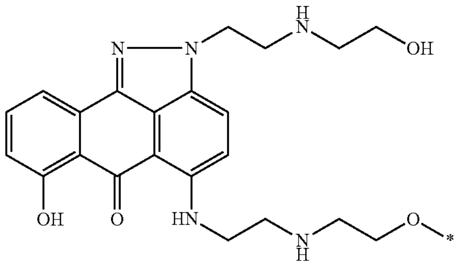 [SMILES: *OCCNCCNc1ccc2c3c(nn2CCNCCO)-c2cccc(O)c2C(=O)c13] a losaxantrone moiety |
| HA24 | 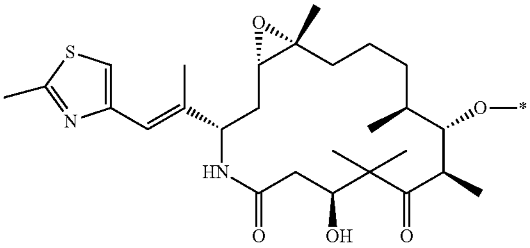 [SMILES: *O[C@H]1[C@@H](C)CCC[C@@]2(C)O[C@H]2C[C@@H](/C(C)=C/c2csc(C)n2)NC(=O)C[C@H](O)C(C)(C)C(=O)[C@@H]1C] an ixabepilone moiety |

TABLE 2

| | $-X^2-X^1-A^1$ Moieties |
|---|---|
| HB1 | $-C(=O)-(CH_2)_{14}-C(=O)-OH$ |
| HB2 | $-C(=O)-(CH_2)_{16}-C(=O)-OH$ |
| HB3 | $-C(=O)-(CH_2)_{18}-C(=O)-OH$ |
| HB4 | $-C(=O)-(CH_2)_7-CH=CH-(CH_2)_7-C(=O)-OH$ |
| HB5 | $-C(=O)-(CH_2)_{14}-C(=O)-O-CH_3$ |
| HB6 | $-C(=O)-(CH_2)_{16}-C(=O)-O-CH_3$ |
| HB7 | $-C(=O)-(CH_2)_{18}-C(=O)-O-CH_3$ |
| HB8 | $-C(=O)-(CH_2)_7-CH=CH-(CH_2)_7-C(=O)-O-CH_3$ |
| HB9 | $-C(=O)-(CH_2)_{14}-CH_3$ |
| HB10 | $-C(=O)-(CH_2)_{16}-CH_3$ |
| HB11 | $-C(=O)-(CH_2)_{18}-CH_3$ |
| HB12 | $-C(=O)-(CH_2)_7-CH=CH-(CH_2)_7-CH_3$ |
| HB13 | $-C(=O)-(CH_2)_2-C(=O)-O-(CH_2)_{15}-C(=O)-OH$ |
| HB14 | $-C(=O)-(CH_2)_2-C(=O)-O-(CH_2)_{17}-C(=O)-OH$ |
| HB15 | $-C(=O)-(CH_2)_2-C(=O)-O-(CH_2)_{19}-C(=O)-OH$ |
| HB16 | $-C(=O)-(CH_2)_2-C(=O)-O-(CH_2)_8-CH=CH-(CH_2)_7-C(=O)-OH$ |
| HB17 | $-C(=O)-CH_2-NH-C(=O)-(CH_2)_{14}-C(=O)-OH$ |
| HB18 | $-C(=O)-CH_2-NH-C(=O)-(CH_2)_{16}-C(=O)-OH$ |
| HB19 | $-C(=O)-CH_2-NH-C(=O)-(CH_2)_{18}-C(=O)-OH$ |
| HB20 | $-C(=O)-CH_2-NH-C(=O)-(CH_2)_7-CH=CH-(CH_2)_7-C(=O)-OH$ |
| HB21 | $-C(=O)-(CH_2)_2-C(=O)-O-[(CH_2)_2-O-]_6C(=O)-(CH_2)_{14}-C(=O)-OH$ |
| HB22 | $-C(=O)-(CH_2)_2-C(=O)-O-[(CH_2)_2-O-]_6C(=O)-(CH_2)_{16}-C(=O)-OH$ |
| HB23 | $-C(=O)-(CH_2)_2-C(=O)-O-[(CH_2)_2-O-]_6C(=O)-(CH_2)_{18}-C(=O)-OH$ |
| HB24 | $-C(=O)-(CH_2)_2-C(=O)-O-[(CH_2)_2-O-]_6C(=O)-(CH_2)_7-CH=CH-(CH_2)_7-C(=O)-OH$ |
| HB25 | $-C(=O)-O-(CH_2)_{15}-C(=O)-OH$ |
| HB26 | $-C(=O)-O-(CH_2)_{17}-C(=O)-OH$ |
| HB27 | $-C(=O)-O-(CH_2)_{19}-C(=O)-OH$ |
| HB28 | $-C(=O)-O-(CH_2)_8-CH=CH-(CH_2)_7-C(=O)-OH$ |
| HB29 | $-C(=O)-NH-(CH_2)_{15}-C(=O)-OH$ |
| HB30 | $-C(=O)-NH-(CH_2)_{17}-C(=O)-OH$ |
| HB31 | $-C(=O)-NH-(CH_2)_{19}-C(=O)-OH$ |
| HB32 | $-C(=O)-NH-(CH_2)_8-CH=CH-(CH_2)_7-C(=O)-OH$ |
| HB33 | $-O-(CH_2)_{15}-C(=O)-OH$ |
| HB34 | $-O-(CH_2)_{17}-C(=O)-OH$ |
| HB35 | $-O-(CH_2)_{19}-C(=O)-OH$ |
| HB36 | $-O-(CH_2)_8-CH=CH-(CH_2)_7-C(=O)-OH$ |
| HB37 | $-NH-(CH_2)_2-O-C(=O)-(CH_2)_{14}-C(=O)-OH$ |
| HB38 | $-NH-(CH_2)_2-O-C(=O)-(CH_2)_{16}-C(=O)-OH$ |

TABLE 2-continued

| | $-X^2-X^1-A^1$ Moieties |
|---|---|
| HB39 | $-NH-(CH_2)_2-O-C(=O)-(CH_2)_{18}-C(=O)-OH$ |
| HB40 | $-NH-(CH_2)_2-O-C(=O)-(CH_2)_7-CH=CH-(CH_2)_7-C(=O)-OH$ |
| HB41 | $-O-(CH_2)_2-O-C(=O)-(CH_2)_{14}-C(=O)-OH$ |
| HB42 | $-O-(CH_2)_2-O-C(=O)-(CH_2)_{16}-C(=O)-OH$ |
| HB43 | $-O-(CH_2)_2-O-C(=O)-(CH_2)_{18}-C(=O)-OH$ |
| HB44 | $-O-(CH_2)_2-O-C(=O)-(CH_2)_7-CH=CH-(CH_2)_7-C(=O)-OH$ |
| HB45 | $-NH-CH_2-C(=O)-O-[(CH_2)_2-O-]_6C(=O)-(CH_2)_{14}-C(=O)-OH$ |
| HB46 | $-NH-CH_2-C(=O)-O-[(CH_2)_2-O-]_6C(=O)-(CH_2)_{16}-C(=O)-OH$ |
| HB47 | $-NH-CH_2-C(=O)-O-[(CH_2)_2-O-]_6C(=O)-(CH_2)_{18}-C(=O)-OH$ |
| HB48 | $-NH-CH_2-C(=O)-O-[(CH_2)_2-O-]_6C(=O)-(CH_2)_7-CH=CH-(CH_2)_7-C(=O)-OH$ |
| HB49 | $-NH-(CH_2)_2-O-C(=O)-(CH_2)_{14}-C(=O)-O-CH_3$ |
| HB50 | $-NH-(CH_2)_2-O-C(=O)-(CH_2)_{16}-C(=O)-O-CH_3$ |
| HB51 | $-NH-(CH_2)_2-O-C(=O)-(CH_2)_{18}-C(=O)-O-CH_3$ |
| HB52 | $-NH-(CH_2)_2-O-C(=O)-(CH_2)_7-CH=CH-(CH_2)_7-C(=O)-O-CH_3$ |
| HB53 | $-CH_2-O-C(=O)-(CH_2)_{14}-C(=O)-OH$ |
| HB54 | $-CH_2-O-C(=O)-(CH_2)_{16}-C(=O)-OH$ |
| HB55 | $-CH_2-O-C(=O)-(CH_2)_{18}-C(=O)-OH$ |
| HB56 | $-CH_2-O-C(=O)-(CH_2)_7-CH=CH-(CH_2)_7-C(=O)-OH$ |
| HB57 | $-CH_2-O-C(=O)-(CH_2)_{14}-C(=O)-O-CH_3$ |
| HB58 | $-CH_2-O-C(=O)-(CH_2)_{16}-C(=O)-O-CH_3$ |
| HB59 | $-CH_2-O-C(=O)-(CH_2)_{18}-C(=O)-O-CH_3$ |
| HB60 | $-CH_2-O-C(=O)-(CH_2)_7-CH=CH-(CH_2)_7-C(=O)-O-CH_3$ |
| HB61 | $-CH_2-O-C(=O)-(CH_2)_{14}-CH_3$ |
| HB62 | $-CH_2-O-C(=O)-(CH_2)_{16}-CH_3$ |
| HB63 | $-CH_2-O-C(=O)-(CH_2)_{18}-CH_3$ |
| HB64 | $-CH_2-O-C(=O)-(CH_2)_7-CH=CH-(CH_2)_7-CH_3$ |
| HB65 | $-CH_2-O-C(=O)-CH_2-NH-C(=O)-(CH_2)_{14}-C(=O)-OH$ |
| HB66 | $-CH_2-O-C(=O)-CH_2-NH-C(=O)-(CH_2)_{16}-C(=O)-OH$ |
| HB67 | $-CH_2-O-C(=O)-CH_2-NH-C(=O)-(CH_2)_{18}-C(=O)-OH$ |
| HB68 | $-CH_2-O-C(=O)-CH_2-NH-C(=O)-(CH_2)_7-CH=CH-(CH_2)_7-C(=O)-OH$ |
| HB69 | $-CH_2-O-C(=O)-(CH_2)_2-C(=O)-O-[(CH_2)_2-O-]_6C(=O)-(CH_2)_{14}-C(=O)-OH$ |
| HB70 | $-CH_2-O-C(=O)-(CH_2)_2-C(=O)-O-[(CH_2)_2-O-]_6C(=O)-(CH_2)_{16}-C(=O)-OH$ |
| HB71 | $-CH_2-O-C(=O)-(CH_2)_2-C(=O)-O-[(CH_2)_2-O-]_6C(=O)-(CH_2)_{18}-C(=O)-OH$ |
| HB72 | $-CH_2-O-C(=O)-(CH_2)_2-C(=O)-O-[(CH_2)_2-O-]_6C(=O)-(CH_2)_7-CH=CH-(CH_2)_7-C(=O)-OH$ |
| HB73 | $-CH_2-O-C(=O)-O-(CH_2)_{15}-C(=O)-OH$ |
| HB74 | $-CH_2-O-C(=O)-O-(CH_2)_{17}-C(=O)-OH$ |
| HB75 | $-CH_2-O-C(=O)-O-(CH_2)_{19}-C(=O)-OH$ |
| HB76 | $-CH_2-O-C(=O)-O-(CH_2)_8-CH=CH-(CH_2)_7-C(=O)-OH$ |
| HB77 | $-CH_2-O-C(=O)-NH-(CH_2)_{15}-C(=O)-OH$ |
| HB78 | $-CH_2-O-C(=O)-NH-(CH_2)_{17}-C(=O)-OH$ |
| HB79 | $-CH_2-O-C(=O)-NH-(CH_2)_{19}-C(=O)-OH$ |
| HB80 | $-CH_2-O-C(=O)-NH-(CH_2)_8-CH=CH-(CH_2)_7-C(=O)-OH$ |
| HB81 | $=N-O-(CH_2)_{15}-C(=O)-OH$ |
| HB82 | $=N-O-(CH_2)_{17}-C(=O)-OH$ |
| HB83 | $=N-O-(CH_2)_{19}-C(=O)-OH$ |
| HB84 | $=N-O-(CH_2)_8-CH=CH-(CH_2)_7-C(=O)-OH$ |
| HB85 | $=N-NH-(CH_2)_{15}-C(=O)-OH$ |
| HB86 | $=N-NH-(CH_2)_{17}-C(=O)-OH$ |
| HB87 | $=N-NH-(CH_2)_{19}-C(=O)-OH$ |
| HB88 | $=N-NH-(CH_2)_8-CH=CH-(CH_2)_7-C(=O)-OH$ |
| HB89 | $=N-O-[(CH_2)_2-O-]_6(CH_2)_{15}-C(=O)-OH$ |
| HB90 | $=N-O-[(CH_2)_2-O-]_6(CH_2)_{17}-C(=O)-OH$ |
| HB91 | $=N-O-[(CH_2)_2-O-]_6(CH_2)_{19}-C(=O)-OH$ |
| HB92 | $=N-O-[(CH_2)_2-O-]_6(CH_2)_8-CH=CH-(CH_2)_7-C(=O)-OH$ |
| HB93 | $-C(=O)-CH_2-O-C(=O)-(CH_2)_{14}-C(=O)-OH$ |
| HB94 | $-C(=O)-CH_2-O-C(=O)-(CH_2)_{16}-C(=O)-OH$ |
| HB95 | $-C(=O)-CH_2-O-C(=O)-(CH_2)_{18}-C(=O)-OH$ |
| HB96 | $-C(=O)-CH_2-O-C(=O)-(CH_2)_7-CH=CH-(CH_2)_7-C(=O)-OH$ |
| HB97 | $-C(=O)-CH(CH_3)-O-C(=O)-(CH_2)_{14}-C(=O)-OH$ |
| HB98 | $-C(=O)-CH(CH_3)-O-C(=O)-(CH_2)_{16}-C(=O)-OH$ |
| HB99 | $-C(=O)-CH(CH_3)-O-C(=O)-(CH_2)_{18}-C(=O)-OH$ |
| HB100 | $-C(=O)-CH(CH_3)-O-C(=O)-(CH_2)_7-CH=CH-(CH_2)_7-C(=O)-OH$ |
| HB101 | $-C(=O)-(CH_2)_5-O-C(=O)-(CH_2)_{14}-C(=O)-OH$ |
| HB102 | $-C(=O)-(CH_2)_5-O-C(=O)-(CH_2)_{16}-C(=O)-OH$ |
| HB103 | $-C(=O)-(CH_2)_5-O-C(=O)-(CH_2)_{18}-C(=O)-OH$ |
| HB104 | $-C(=O)-(CH_2)_5-O-C(=O)-(CH_2)_7-CH=CH-(CH_2)_7-C(=O)-OH$ |

TABLE 3

| Compound No. | $A^2$-Moiety | $-X^2-X^1-A^1$ Moiety |
|---|---|---|
| 1-44 | HA1 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 45-88 | HA2 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 89-132 | HA9 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 133-176 | HA12 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 177-220 | HA14 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 221-264 | HA15 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 265-308 | HA16 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 309-352 | HA19 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 353-396 | HA20 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 397-440 | HA21 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 441-484 | HA22 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 485-528 | HA23 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 529-572 | HA24 | HB1, HB2, HB3, HB4, HB5, HB6, HB7, HB8, HB9, HB10, HB11, HB12, HB13, HB14, HB15, HB16, HB17, HB18, HB19, HB20, HB21, HB22, HB23, HB24, HB25, HB26, HB27, HB28, HB29, HB30, HB31, HB32, HB93, HB94, HB95, HB96, HB97, HB98, HB99, HB100, HB101, HB102, HB103, HB104, respectively |
| 573-592 | HA5 | HB33, HB34, HB35, HB36, HB37, HB38, HB39, HB40, HB41, HB42, HB43, HB44, HB45, HB46, HB47, HB48, HB49, HB50, HB51, HB52, respectively |
| 593-612 | HA6 | HB33, HB34, HB35, HB36, HB37, HB38, HB39, HB40, HB41, HB42, HB43, HB44, HB45, HB46, HB47, HB48, HB49, HB50, HB51, HB52, respectively |
| 613-632 | HA7 | HB33, HB34, HB35, HB36, HB37, HB38, HB39, HB40, HB41, HB42, HB43, HB44, HB45, HB46, HB47, HB48, HB49, HB50, HB51, HB52, respectively |
| 633-652 | HA8 | HB33, HB34, HB35, HB36, HB37, HB38, HB39, HB40, HB41, HB42, HB43, HB44, HB45, HB46, HB47, HB48, HB49, HB50, HB51, HB52, respectively |
| 653-672 | HA11 | HB33, HB34, HB35, HB36, HB37, HB38, HB39, HB40, HB41, HB42, HB43, HB44, HB45, HB46, HB47, HB48, HB49, HB50, HB51, HB52, respectively |
| 673-692 | HA17 | HB33, HB34, HB35, HB36, HB37, HB38, HB39, HB40, HB41, HB42, HB43, HB44, HB45, HB46, HB47, HB48, HB49, HB50, HB51, HB52, respectively |
| 693-720 | HA3 | HB53, HB54, HB55, HB56, HB57, HB58, HB59, HB60, HB61, HB62, HB63, HB64, HB65, HB66, HB67, HB68, HB69, HB70, HB71, HB72, HB73, HB74, HB75, HB76, HB77, HB78, HB79, HB80, respectively |
| 721-748 | HA4 | HB53, HB54, HB55, HB56, HB57, HB58, HB59, HB60, HB61, HB62, HB63, HB64, HB65, HB66, HB67, HB68, HB69, HB70, HB71, HB72, HB73, HB74, HB75, HB76, HB77, HB78, HB79, HB80, respectively |
| 749-760 | HA10 | HB81, HB82, HB83, HB84, HB85, HB86, HB87, HB88, HB89, HB90, HB91, HB92, respectively |
| 761-772 | HA13 | HB81, HB82, HB83, HB84, HB85, HB86, HB87, HB88, HB89, HB90, HB91, HB92, respectively |
| 773-784 | HA18 | HB81, HB82, HB83, HB84, HB85, HB86, HB87, HB88, HB89, HB90, HB91, HB92, respectively |

Pharmaceutical Compositions

In certain aspects, the compounds of any of the preceding embodiments may be formulated into pharmaceutical compositions in any suitable manner. In general, as compounds for the treatment of cancer, such pharmaceutical formulations are aqueous formulations suitable for parenteral administration, such as intravenous or intra-arterial administration.

In at least one aspect, the disclosure provides pharmaceutical compositions that include one or more compounds of formula (I) (according to any of the foregoing embodiments) and a protein. In some embodiments, the protein is an albumin or an albumin mimetic. In some such embodiments, the protein is human serum albumin (HSA) or a mimetic thereof, i.e., a protein whose sequence is at least 50% equivalent to that of HSA, or at least 60% equivalent to that of HSA, or at least 70% equivalent to that of HSA, or at least 80% equivalent to that of HSA, or at least 90% equivalent to that of HSA, or at least 95% equivalent to that of HSA, at least 97% equivalent to that of HSA, at least 99% equivalent to that of HSA. In some embodiments, the protein is human serum albumin.

In certain embodiments of any of the foregoing embodiments, the pharmaceutical composition also includes a carrier, such as a liquid carrier. In some embodiments, the carrier includes water. For example, in some such embodiments, water makes up at least 50% by volume, or at least 60% by volume, or at least 70% by volume, or at least 80% by volume, or at least 90% by volume, based on the total volume of liquid materials in the pharmaceutical composition. The carrier can also include other liquid ingredients, such as liquid ingredients commonly included in aqueous pharmaceutical formulations for parenteral administration.

In certain embodiments having an aqueous carrier, the compounds of formula (I) bind non-covalently to the protein in the pharmaceutical formulation. In some embodiments, the compound of formula (I) and the protein (e.g., human serum albumin) are non-covalently associated with each other with a binding constant ($K_b$) of at least $10^2$ $M^{-1}$, or at least $10^3$ $M^{-1}$, or at least $10^4$ $M^{-1}$, or at least $10^5$ $M^{-1}$ at 25° C. in the aqueous composition.

In some embodiments having an aqueous carrier, the compound of formula (I) and the protein are solvated by the carrier. In some such embodiments, at least 90% by weight, or at least 95% by weight, or at least 97% by weight, or at least 98% by weight, or at least 99% by weight of the compounds of formula (I) in the composition are bound non-covalently to the protein with a binding constant ($K_b$) of at least $10^2$ $M^{-1}$, or at least $10^3$ $M^{-1}$, or at least $10^4$ $M^{-1}$, or at least $10^5$ $M^{-1}$ at 25° C. in the aqueous composition. In some further such embodiments, the composition is substantially free of agglomerates or nanoparticles. For example, in some embodiments of any of the aforementioned embodiments, no more than 5% by weight, or no more than 4% by weight, or no more than 3% by weight, or no more than 2% by weight, or no more than 1% by weight of the protein-compound (i.e., non-covalently bound conjugates between the protein and one or more compounds of formula (I)) in the aqueous composition have a radius greater than 7 nm, or a radius greater than 5 nm, or a radius greater than 4 nm, as measured by dynamic light scattering.

The compound of formula (I) can have any suitable molar ratio to the protein in the formulation. For example, in some embodiments of any of the foregoing embodiments, the molar ratio of the compound of formula (I) to the protein ranges from 1:10 to 20:1, or from 1:5 to 15:1, or from 1:2 to 10:1. In some embodiments of any of the foregoing embodiments, the molar ratio of the compound of formula (I) to the protein is about 1:1, or is about 2:1, or is about 3:1, or is about 4:1, or is about 5:1, or is about 6:1, or is about 7:1, wherein the term "about," in this instance means ±0.5:1, such that "about 5:1" refers to a range from 4.5:1 to 5.5:1.

In at least one aspect, the disclosure provides pharmaceutical compositions that include: a compound, which comprises a cytotoxic drug moiety and a protein binding moiety; a protein, wherein the protein is an albumin or an albumin mimetic; and a carrier, which comprises water.

In some embodiments, the protein is human serum albumin (HSA) or a mimetic thereof, i.e., a protein whose sequence is at least 50% equivalent to that of HSA, or at least 60% equivalent to that of HSA, or at least 70% equivalent to that of HSA, or at least 80% equivalent to that of HSA, or at least 90% equivalent to that of HSA, or at least 95% equivalent to that of HSA, at least 97% equivalent to that of HSA, at least 99% equivalent to that of HSA. In some embodiments, the protein is human serum albumin.

As noted above, in some embodiments, the carrier includes water. For example, in some such embodiments, water makes up at least 50% by volume, or at least 60% by volume, or at least 70% by volume, or at least 80% by volume, or at least 90% by volume, based on the total volume of liquid materials in the pharmaceutical composition. The carrier can also include other liquid ingredients, such as liquid ingredients commonly included in aqueous pharmaceutical formulations for parenteral administration.

In certain embodiments, the compounds bind non-covalently to the protein in the pharmaceutical formulation. In some embodiments, the compound and the protein (e.g., human serum albumin) are non-covalently associated with each other with a binding constant ($K_b$) of at least $10^2$ $M^{-1}$, or at least $10^3$ $M^{-1}$, or at least $10^4$ $M^{-1}$, or at least $10^5$ $M^{-1}$ at 25° C. in the aqueous composition.

In some embodiments having an aqueous carrier, the compound and the protein are solvated by the carrier. In some such embodiments, at least 90% by weight, or at least 95% by weight, or at least 97% by weight, or at least 98% by weight, or at least 99% by weight of the compounds of formula (I) in the composition are bound non-covalently to the protein with a binding constant ($K_b$) of at least $10^2$ $M^{-1}$, or at least $10^3$ $M^{-1}$, or at least $10^4$ $M^{-1}$, or at least $10^5$ $M^{-1}$ at 25° C. in the aqueous composition. In some further such embodiments, the composition is substantially free of agglomerates or nanoparticles. For example, in some embodiments of any of the aforementioned embodiments, no more than 5% by weight, or no more than 4% by weight, or no more than 3% by weight, or no more than 2% by weight, or no more than 1% by weight of the protein-compound (i.e., non-covalently bound conjugates between the protein and one or more compounds of formula (I)) in the aqueous composition have a radius greater than 7 nm, or a radius greater than 5 nm, or a radius greater than 4 nm, as measured by dynamic light scattering.

The compound of formula (I) can have any suitable molar ratio to the protein in the formulation. For example, in some embodiments of any of the foregoing embodiments, the molar ratio of the compound of formula (I) to the protein ranges from 1:10 to 20:1, or from 1:5 to 15:1, or from 1:2 to 10:1. In some embodiments of any of the foregoing embodiments, the molar ratio of the compound of formula (I) to the protein is about 1:1, or is about 2:1, or is about 3:1, or is about 4:1, or is about 5:1, or is about 6:1, or is about 7:1, wherein the term "about," in this instance means ±0.5:1, such that "about 5:1" refers to a range from 4.5:1 to 5.5:1.

The pharmaceutical compositions of any of the foregoing aspects and embodiments can also include certain additional ingredients, such as those commonly employed in pharmaceutical compositions for parenteral administration.

Methods and Uses

The compounds or compositions of any of the foregoing embodiments are useful in the treatment of cancer and related disorders. Therefore, these compounds and compositions can be used for administration to a subject who has or has had a cancerous tumor.

Thus, in certain aspects, the disclosure provides methods of treating cancer, including administering to a subject a compound or composition of any of the foregoing aspects and embodiments. In some embodiments, the subject is a human. In some embodiments, the subject is a subject in need of such treatment, e.g., a human in need of such treatment.

In some aspects, the disclosure provides methods of inducing apoptosis in a cancer cell, including contacting the cancer cell with a compound or composition of any of the foregoing aspects and embodiments.

In some aspects, the disclosure provides methods of inhibiting proliferation of a cancerous tumor, including contacting the cancerous tumor with a compound or composition of any of the foregoing aspects and embodiments.

In some aspects, the disclosure provides uses of a compound or composition of any of the foregoing aspects and embodiments as a medicament.

In some aspects, the disclosure provides uses of a compound or composition of any of the foregoing aspects and embodiments for treating cancer.

In some aspects, the disclosure provides uses of a compound of any of the foregoing aspects and embodiments in the manufacture of a medicament.

In some aspects, the disclosure provides uses of a compound of any of the foregoing aspects and embodiments in the manufacture of a medicament for treating cancer.

EXAMPLES

The following examples show certain illustrative embodiments of the compounds, compositions, and methods disclosed herein. These examples are not to be taken as limiting in any way. Nor should the examples be taken as expressing any preferred embodiments, or as indicating any direction for further research.

The examples may use abbreviations for certain common chemicals. The following abbreviations refer to the compounds indicated.

DMF=Dimethylformamide

DCM=Dichloromethane

NMR=Nuclear magnetic resonance

HPLC=High-performance liquid chromatography

RP-HLPC=Reverse-phase high-performance liquid chromatography

LRMS=Liquid chromatography/low-resolution mass spectrometry

HRMS=Liquid chromatography/high-resolution mass spectrometry

Tips=Triisopropylsilyl

DMAP=4-(Dimethylamino)pyridine

EDC=1-Ethyl-3-(3-dimethylaminopropyl)carbodiimide

THF=Tetrahydrofuran

Dipea=N,N-diisopropylethylamine

HATU=1-[Bis(dimethylamino)methylene]-1H-1,2,3-triazolo-[4,5-b]pyridinium 3-oxide hexafluorophosphate DCC=N,N'-dicyclohexylcarbodiimide HSA=Human serum albumin

Example 1

Mono-Tips Protected C18 Diacid

To a solution of the diacid (10 g) in dry DMF (150 mL) at 60° C. was added triisopropylsilyl chloride (6.68 mL). To the stirred solution was added dropwise freshly distilled triethylamine (4.35 mL). The reaction was stirred overnight under nitrogen atmosphere then the solution was cooled to room temperature, filtered and concentrated to dryness. Dichloromethane (150 mL) was added to the solid and the round bottom sonicated. The solid was filtered off and the solvent was removed under vacuum. The residue was purified by column chromatography (2.5% THF in DCM) to give a clear oil. 6.1 g, 41% yield. LRMS—471.32 $[M+H]^+$, HRMS—Theoretical=471.3864, Observed=471.3861. $^1H$ NMR ($CDCl_3$): δ(ppm) 1.06-1.09 (m, 21H), 1.2-1.4 (m, 24H), 1.55-1.70 (m, 4H), 2.30-2.40 (m, 4H).

Example 2

Paclitaxel-C18 Diacid Conjugate (PTX-FA18)

To a stirring solution of paclitaxel (500 mg) in dry DCM (50 mL) at 0° C. was added DMAP (231 mg). After 5 minutes, EDC (137 mg) was added. After an additional 5 minutes, was added Mono-Tips Protected C18 Diacid (791 mg) and the resulting solution allowed to stir, and warm to room temperature overnight. The crude reaction mixture was then transferred to a separatory funnel and washed with water (3×50 mL), saturated NaCl (3×50 mL) and 0.1M HCl (3×50 mL). The organic phase was dried over $MgSO_4$, and rotovapped to afford a yellowish-white solid. To remove the TIPS protecting group, the solid was taken up in THF and $Bu_4NF$ (1.2 g, 0.0046 mol) was added and stirred. After 18 h, excess AMBERLITE ion exchange resin and excess $CaCO_3$ were added to the reaction mixture. After 1 h, the solution was filtered and the filtrate concentrated to a free-flowing oil. The oil was dissolved in 50 mL DCM, and upon addition of water a white precipitate crashed out. The reaction mixture was filtered and transferred to a separatory funnel, where it was extracted with water (3×50 mL). The organic phase was dried over $MgSO_4$, filtered, and concentrated to afford a clear/white, glassy solid. 521 mg, 81% yield. MS—Theoretical=1147.59 $[M-H]^-$, Observed=1148.38. $^1H$ NMR ($CDCl_3$): δ(ppm) 0.08-1.10 (m, 21H), 1.2-1.4 (m, 24H), 1.55-1.64 (m, 4H), 1.65-1.7 (m, 2H), 1.8-1.95 (m, 4H), 1.95-1.05 (m, 2H), 2.1-2.15 (m, 4H), 2.25-2.40 (m, 6H), 2.4-2.5 (m, 2H), 2.5-2.55 (m, 1H), 3.7 (s, 1H), 3.75-3.95 (m, 3H), 4.1 (m, 1H), 4.2 (m, 1H), 4.3 (m, 1H), 4.4 (m, 1H), 4.7 (m, 1H), 4.95 (m, 1H), 5.5 (m, 1H), 5.7 (m, 1H), 5.8 (m, 1H), 6.2-6.3 (m, 2H), 6.8 (m, 1H), 6.97 (m, 1H), 7.05 (m, 1H), 7.3-7.45 (m, 5H), 7.45-7.55 (m, 4H), 7.6 (m, 1H), 7.75 (m, 2H), 8.1-8.2 (m, 2H).

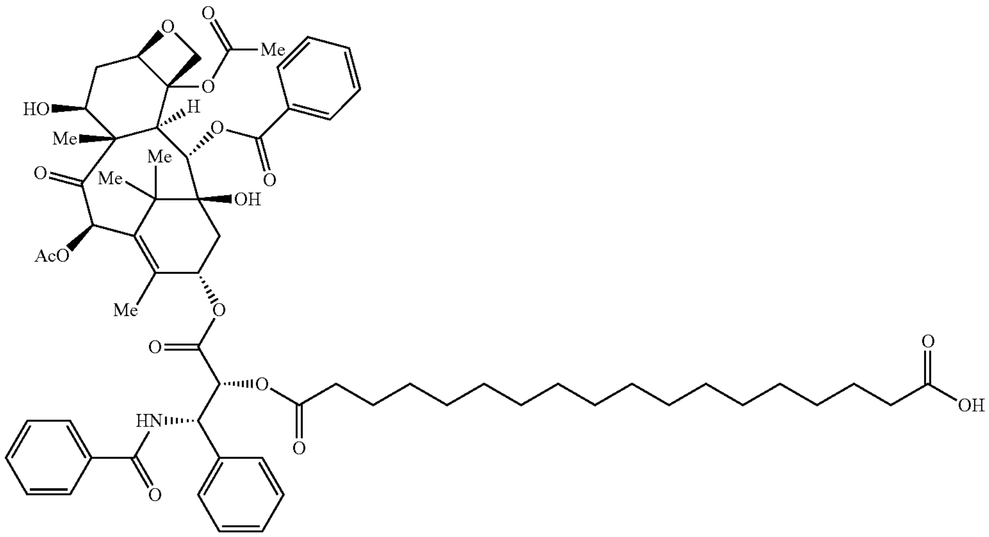 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCCCCCCCCCCCCCCCC(=O)O)[C@@H](NC(=O)c4ccccc4)c4ccccc4)C(C)=C1C3(C)C)[C@]1(OC(C)=O)CO[C@@H]1C[C@@H]2O]

Example 3

Paclitaxel-C16 Diacid Conjugate (PTX-FA16)

Hexadecanedioic acid (250 mg), paclitaxel (372 mg), EDC (251 mg) and DMAP (160 mg) were dissolved in DMF (5 mL) and stirred under a nitrogen atmosphere overnight. The reaction mixture was concentrated to dryness, the residue dissolved in chloroform and washed with water (3×20 mL). The organic layer was dried $Na_2SO_4$, filtered and concentrated to dryness. The solid was purified by preparative HPLC to give the conjugate as a white solid. $^1$HNMR, $CDCl_3$, 8.14 (2H, d), 7.74 (2H, d), 7.62 (1H, t), (7.55-7.30, 9H, m), 6.94 (1H, m), 6.31 (1H, s), 6.27 (1H, t), 5.95 (1H, m), 5.69 (1H, d), 5.51 (1H, m), 4.99 (1H, m) 4.45 (1H, m), 4.32 (1H, m), 4.21 (1H, m), 3.82 (1H, m), 2.60-1.00 (51H, m). LRMS, ESI, 1121.03 $[M-H]^-$.

Example 4

Paclitaxel-C20 Diacid Conjugate (PTX-FA20)

Eicosanedioic acid (160 mg), paclitaxel (200 mg), EDC (135 mg) and DMAP (86 mg) were dissolved in DMF (2 mL), stirred under a nitrogen atmosphere overnight, then concentrated to dryness. The solid was purified by preparative HPLC (65%-95% ACN) to give the conjugate as a white solid. $^1$HNMR, $CDCl_3$, 8.14 (2H, d), 7.74 (2H, d), 7.62 (1H, t), (7.56-7.30, 9H, m), 6.95 (1H, m), 6.31 (1H, s), 6.27 (1H, t), 5.96 (1H, m), 5.70 (1H, d), 5.51 (1H, m), 4.99 (1H, m) 4.45 (1H, m), 4.33 (1H, m), 4.22 (1H, m), 3.82 (1H, m), 2.60-1.00 (59H, m). LRMS, ESI, 1290.67 $[M-H+TFA]^-$.

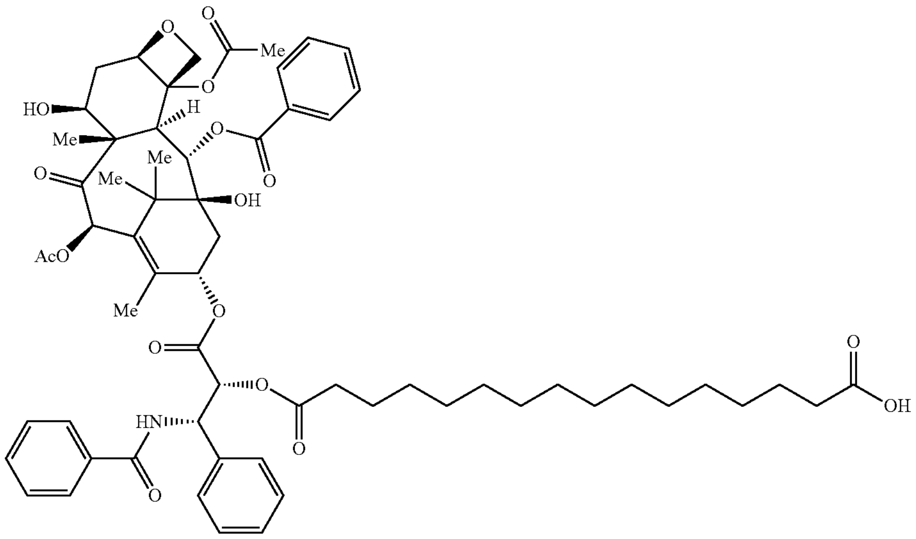 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCCCCCCCCCCCCCC(=O)O)[C@@H](NC(=O)c4ccccc4)c4ccccc4)C(C)=C1C3(C)C)[C@]1(OC(C)=O)CO[C@@H]1C[C@@H]2O]

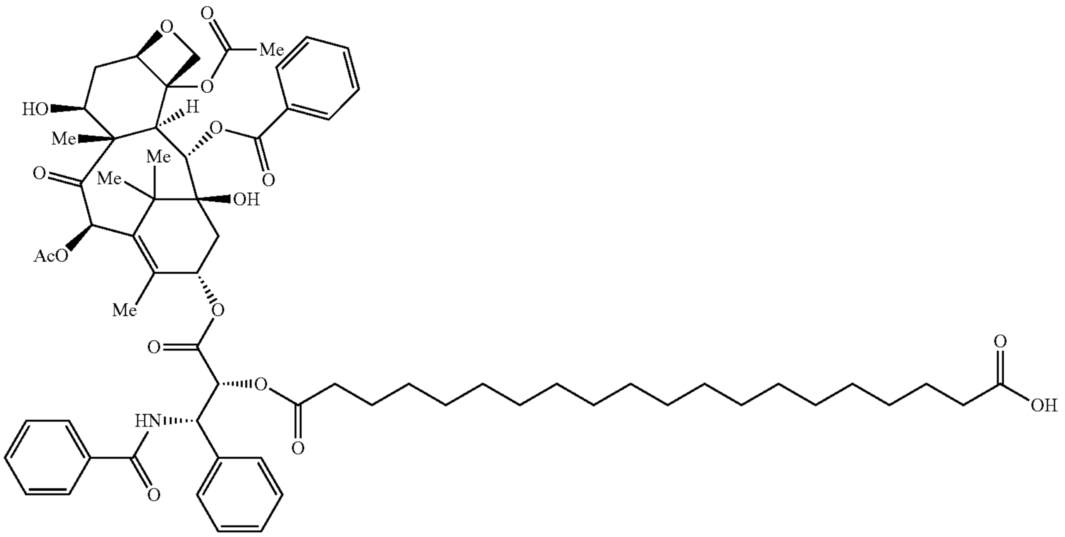 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCCCCCCCCCCCCCCCCCC(=O)O)[C@@H](NC(=O)c4ccccc4)c4ccccc4)C(C)=C1C3(C)C)[C@]1(OC(C)=O)CO[C@@H]1C[C@@H]2O]

Example 5

Paclitaxel-uC18 Diacid Conjugate (PTX-FAu18)

Octadec-9-enedioic acid (37 mg; 85% trans/15% cis), paclitaxel (200 mg), EDC (45 mg) and DMAP (29 mg) were dissolved in DMF (2 mL), stirred under a nitrogen atmosphere overnight, then concentrated to dryness. The solid was purified by preparative HPLC (65%-95% ACN) to give the conjugate as a white solid. $^1$HNMR, $CDCl_3$, 8.14 (2H, d), 7.74 (2H, d), 7.62 (1H, t), (7.55-7.30, 9H, m), 7.03 (1H, m), 6.30 (1H, s), 6.27 (1H, t), 5.97 (1H, m), 5.69 (1H, d), 5.52 (1H, m), 5.37 (2H, m), 4.99 (1H, m) 4.45 (1H, m), 4.33 (1H, m), 4.21 (1H, m), 3.82 (1H, m), 2.60-1.00 (51H, m). LRMS, ESI, 1146.72 [M−H]$^-$.

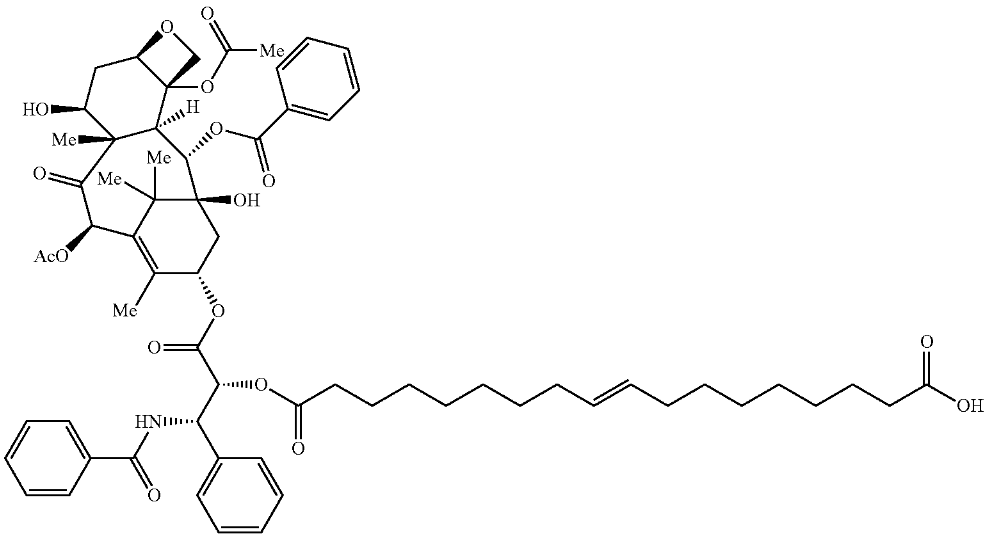 [SMILES: CC(=O)O[C@H]1C(=O)[C@@]2(C)[C@H]([C@H](OC(=O)c3ccccc3)[C@]3(O)C[C@H](OC(=O)[C@H](OC(=O)CCCCCCC/C=C/CCCCCCCC(=O)O)[C@@H](NC(=O)c4ccccc4)c4ccccc4)C(C)=C1C3(C)C)[C@]1(OC(C)=O)CO[C@@H]1C[C@@H]2O]

Example 6

Methotrexate-C18 Diacid Conjugate (MTX-FA18)

To a solution of methotrexate (66 mg) in DMF (1 mL) was added Dipea (50 μL) followed by HATU (55 mg), after stirring for 3 minutes 18-(2-aminoethoxy)-18-oxooctadecanoic acid (57 mg) was added and the reaction stirred overnight under a nitrogen atmosphere. The solution was concentrated to dryness and the resulting solid purified by preparative HPLC (40%-50% ACN) to give the conjugate as a yellow solid. $^1$HNMR, DMF-d7, 9.33 (1H, bs), 9.17 (1H, bs), 8.82 (1H, s), 8.13 (1H, m), 7.88 (2H, m), 6.91 (2H, m), 4.95 (2H, s), 4.10 (1H, m), 3.33 (3H, s), 2.45-2.0 (12H, m), 1.55 (4H, m), 1.27, (24H, m). LRMS, ESI, 792.57 [M−H]$^-$.

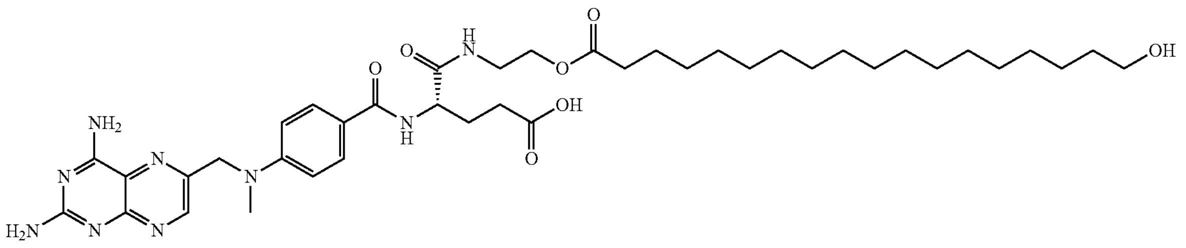

+

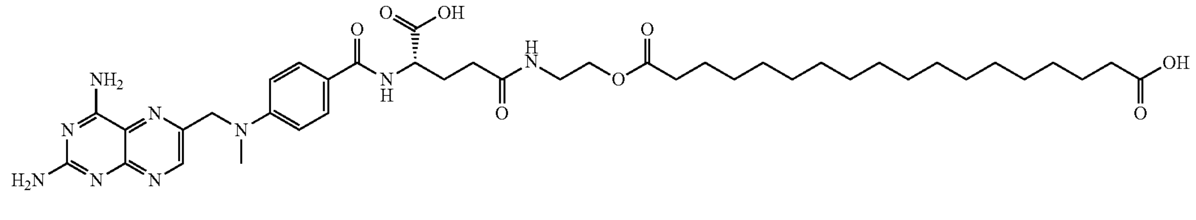

Example 7

Carbonate-modified Intermediate

To a solution of methyl 18-hydroxyoctadecanoate (320 mg) and pyridine (222 μL) in $CHCl_3$/DMF (8:2) was slowly added the p-nitrophenyl chloroformate (246 mmol). The reaction mixture was stirred under a nitrogen atmosphere overnight then transferred to a separatory funnel and washed with water (×3). The organic layer was dried with $Na_2SO_4$, filtered and concentrated to dryness. The solid was purified by column chromatography (100% $CHCl_3$) to give a white solid. $^1$HNMR, $CDCl_3$, 8.29 (2H, d), 7.39 (2H, d), 4.30 (2H, t), 3.67 (3H, s), 2.31 (2H, t), 1.76 (2H, m), 1.70-1.58 (2H, m), 1.42 (3H, t), 1.26 (27H, m). LRMS, ESI, 480.47 $[M+H]^+$.

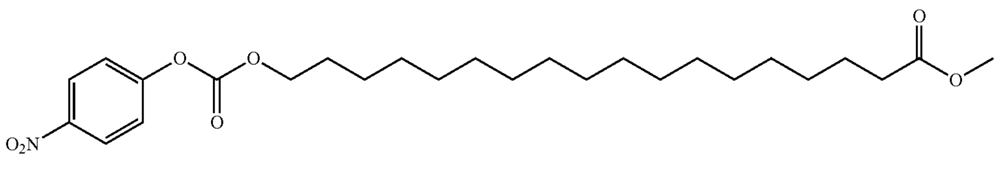 [SMILES: COC(=O)CCCCCCCCCCCCCCCCCOC(=O)Oc1ccc([N+](=O)[O-])cc1]

Example 8

Doxorubicin-C18 Acid-Ester Carbamate Conjugate (DOX-FAE18-Cm)

To a solution of doxorubicin hydrochloride (50 mg) in dry DMF (1 mL) was added triethylamine (30 mL) followed by methyl 18-(((4-nitrophenoxy)carbonyl)oxy)octadecanoate (50 mg). The reaction was stirred under a nitrogen atmosphere overnight then concentrated to dryness. The residue was dissolved in chloroform, washed with water (×3) and the organic layer dried with $Na_2SO_4$, filtered and concentrated to dryness. The red solid was purified by column chromatography (10% toluene in DCM) to give a red solid. $^1$HNMR, $CDCl_3$, 8.02 (1H, m), 7.78 (1H, m), 7.39 (1H, m), 6.80 (1H, m), 5.50 (1H, m), 5.28 (1H, m), 5.06 (1H, m), 4.76 (2H, s), 4.56 (1H, m), 4.20-4.05 (4H, m), 3.98 (2H, m), 3.85 (1H, m), 3.67 (3H, s) 3.25 (1H, d), 3.04 (1H, m), 2.98 (1H, d), 2.36-1.20 (37H, m). LRMS, ESI, 882.90 $[M-H]^-$.

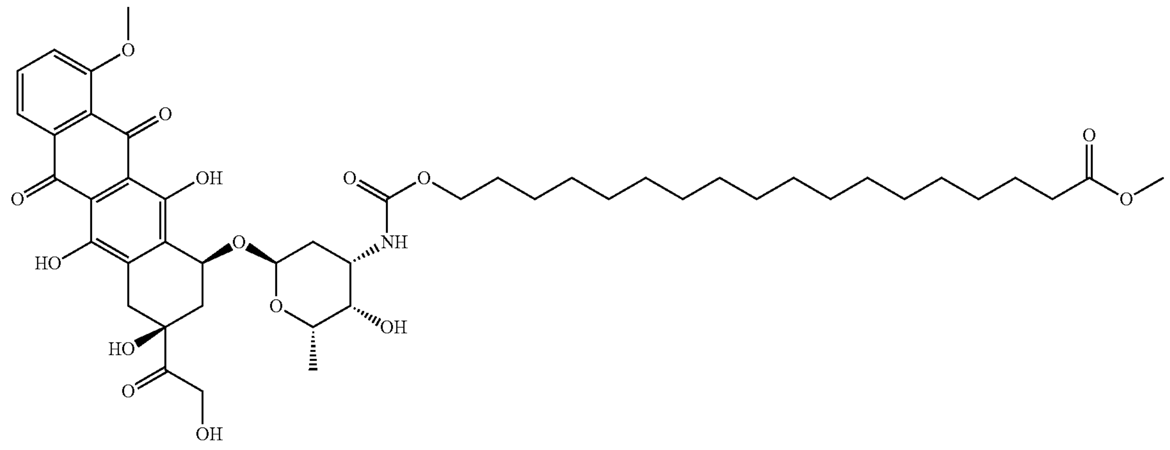 [SMILES: COC(=O)CCCCCCCCCCCCCCCCCOC(=O)N[C@H]1C[C@H](O[C@H]2C[C@](O)(C(=O)CO)Cc3c(O)c4c(c(O)c32)C(=O)c2c(OC)cccc2C4=O)O[C@@H](C)[C@H]1O]

Example 9

Pentafluorophenol Intermediate

To a solution of 18-methoxy-18-oxooctadecanoic acid (250 mg), pentafluorophenol (140 mg), and DMAP (23 mg) in ethyl acetate (10 mL) was added a solution of DCC (157 mg) in ethyl acetate (2 mL). The reaction was stirred under a nitrogen atmosphere overnight. The resulting precipitate was removed by filtration and the solvent removed under reduced pressure to give a white solid. $^1$HNMR, $CDCl_3$, 3.67 (3H, s), 2.31 (2H, t), 1.78 (2H, m), 1.62 (2H, m), 1.42 (2H, m), 1.26 (22H, m). LRMS, ESI, 517.40 $[M+Na]^+$.

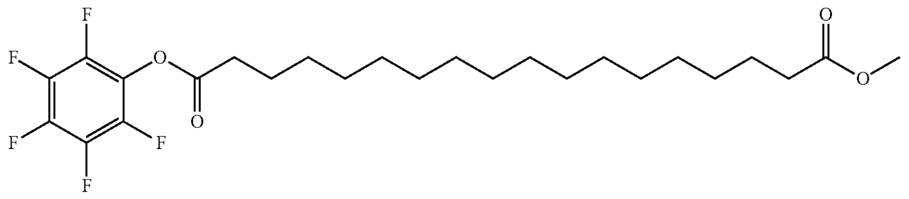 [SMILES: COC(=O)CCCCCCCCCCCCCCCCC(=O)Oc1c(F)c(F)c(F)c(F)c1F]

Example 10

Amino Acid-modified Intermediate

A solution of 1-methyl 18-(perfluorophenyl) octadecanedioate (250 mg), 6-aminohexanoic acid (66 mg) and triethylamine (141 μL) in DMF (5 mL) was heated at 60° C. with stirring under a nitrogen atmosphere for 48 hrs. The reaction mixture was cooled and concentrated under reduced pressure. The residue was dissolved in chloroform and washed with 10% HCl (×3), the organic layer was dried with $Na_2SO_4$, filtered and concentrated to dryness to give a tan solid. $^1$HNMR, $CDCl_3$, 7.72 (1H, m), 3.64 (3H, s), 3.14 (2H, m), 2.40-2.20 (4H, m), 2.14 (2H, t), 1.60-1.40 (8H, m), 1.26 (26H, m). LRMS, ESI, 442.56 $[M+H]^+$.

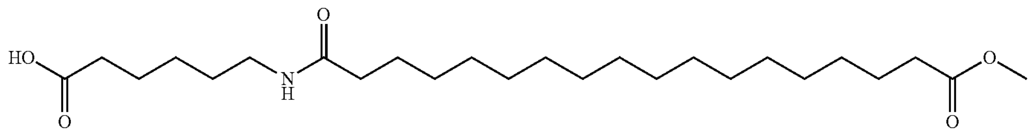 [SMILES: COC(=O)CCCCCCCCCCCCCCCCC(=O)NCCCCCC(=O)O]

Example 11

Paclitaxel-C18 Diacid Conjugate+Amino Acid Spacer (PTX-FAE18-Aa)

To a solution of 6-(18-methoxy-18-oxooctadecanamido) hexanoic acid (103 mg), Paclitaxel (299 mg) and DMAP (43 mg) in DMF (2 mL) was added EDC (67 mg). The reaction mixture was stirred under a nitrogen atmosphere overnight then concentrated to dryness. The residue was dissolved in chloroform and washed with 0.1M HCl (3×). The organic layer was dried with $Na_2SO_4$, filtered and concentrated to dryness. The solid was purified by preparative HPLC (65%-95% ACN) to give the conjugate as a white solid. $^1$HNMR, $CDCl_3$, 8.14 (2H, d), 7.75 (2H, d), 7.62 (1H, m), (7.55-7.30, 10H, m), 7.11 (1H, m), 6.30 (1H, s), 6.23 (1H, m), 5.95 (1H, m), 5.68 (1H, m), 5.50 (1H, m), 4.98 (1H, m) 4.45 (1H, m), 4.32 (1H, m), 4.21 (1H, m), 3.82 (1H, m), 3.67 (3H, s), 3.18 (2H, m), 2.60-1.00 (62H, m). LRMS, ESI, 1312.52 $[M-H+Cl]^-$.

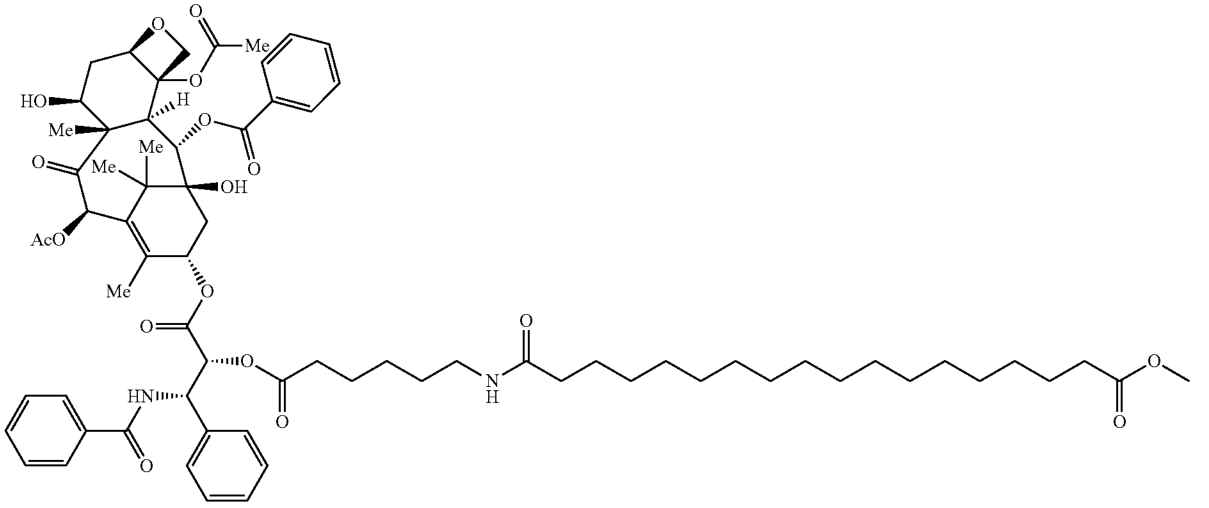 [SMILES: COC(=O)CCCCCCCCCCCCCCCCC(=O)NCCCCCC(=O)O[C@@H](C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](OC(C)=O)C(=C1C)C2(C)C)[C@@H](NC(=O)c1ccccc1)c1ccccc1]

Example 12

Camptothecin-C18 Diacid Conjugate (CPT-FA18)

Camptothecin was stirred with the octadecanedioic acid in DMF, along with EDC and DMAP in excess. After reaction was complete, reaction solution was concentrated, brought up in DCM, then washed 2× 1M HCl and 1×$H_2O$. The organic layer was dried over $MgSO_4$, filtered and concentrated. Crude FA-CPT was purified first by flash chromatography using a gradient elution (100% DCM→10% methanol in DCM); then purified by prep RP-HPLC using a 70-90% acetonitrile in water+0.1% TFA gradient, monitoring at 260 nm. The purified product was lyophilized to remove the HPLC solvents, leaving a yellow-tinted powder. $^1$HNMR, $CDCl_3$, 8.41 (s, 1H), 8.23 (d, 1H, J=8.4 Hz), 7.95 (d, 1H, J=8.1 Hz), 7.84 (t, 1H, J=8.5 Hz), 7.68 (t, 1H, 7.1 Hz), 7.26 (s, 1H), 5.68 (d, 1H, J=17.2 Hz), 5.42 (d, 1H, J=17.2 Hz), 5.31 (s, 2H), 2.49 (m, 2H), 2.35 (t, 2H, J=8.0 Hz), 2.29 (m, 1H), 2.17 (m, 1H), 1.70-1.59 (m, 4H), 1.39-1.11 (m, 24H), 0.98 (t, 3H, 7.4 HZ). LRMS, ESI, 644.83 $[M-H]^-$.

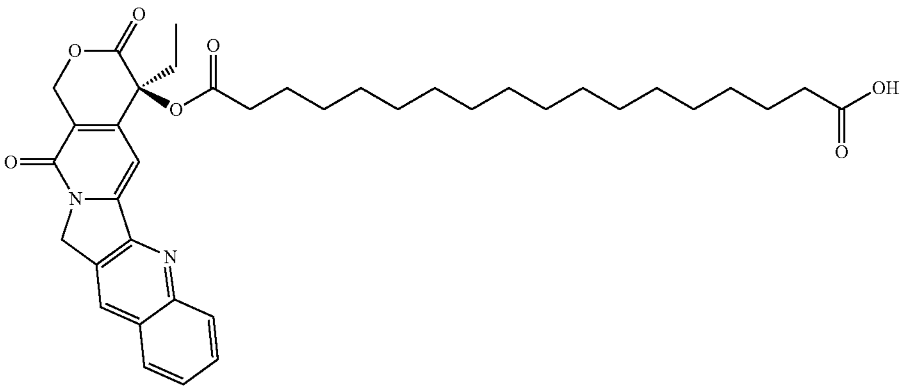 [SMILES: CC[C@@]1(OC(=O)CCCCCCCCCCCCCCCCC(=O)O)C(=O)OCc2c1cc1n(c2=O)Cc2cc3ccccc3nc2-1]

Example 13

Ixabepilone-C18 Diacid Conjugate (IXB-FA18)

To a stirring solution of ixabepilone (500 mg) in dry DCM (50 mL) at 0° C. is added DMAP (231 mg). After 5 minutes, EDC (137 mg) is added. After an additional 5 minutes, is added Mono-Tips Protected C18 Diacid (791 mg) and the resulting solution allowed to stir, and warm to room temperature overnight. The crude reaction mixture is then transferred to a separatory funnel and washed with water (3x50 mL), saturated NaCl (3x50 mL) and 0.1M HCl (3x50 mL). The organic phase is dried over $MgSO_4$, and rotovapped to afford a yellowish-white solid. To remove the TIPS protecting group, the solid is taken up in THF and $Bu_4NF$ (1.2 g) is added and stirred. After 18 h, excess AMBERLITE ion exchange resin and excess $CaCO_3$ are added to the reaction mixture. After 1 h, the solution is filtered and the filtrate is concentrated to a free-flowing oil. The oil is dissolved in 50 mL DCM, and upon addition of water a white precipitate forms. The reaction mixture is filtered and transferred to a separatory funnel, where it is extracted with water (3x50 mL). The organic phase is dried over $MgSO_4$, filtered, and is concentrated to afford a solid. MS—Theoretical=803.16 $[M-H]^-$.

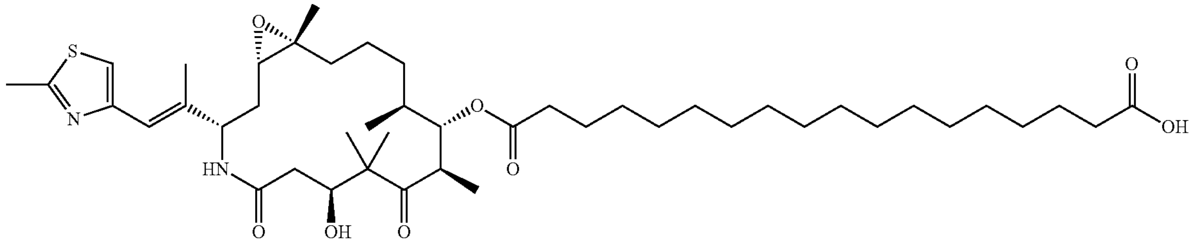 [SMILES: C/C(=C\c1csc(C)n1)[C@@H]1C[C@@H]2O[C@]2(C)CCC[C@H](C)[C@H](OC(=O)CCCCCCCCCCCCCCCCC(=O)O)[C@@H](C)C(=O)C(C)(C)[C@@H](O)CC(=O)N1]

Example 14

Complexation of PTX-FA to Human Serum Albumin (PTX-FA-HSA)

Human serum albumin (HSA) was dissolved in distilled water to yield a 4% (w/v) solution (1000 uL, $7.19\times10^{-4}$ M). To this was rapidly added a stock solution of PTX-FA (100 uL, 0.0144 M). The resulting solution was sonicated for 10 seconds, snap frozen, and lyophilized. The lyophilized powder was resuspended in 1.0 mL 1× DPBS.

Example 15

Data and Results: In Vivo Efficacy

Equivalent doses (240 mg/kg with respect to paclitaxel content) of PTX-FA-HSA was given to tumor-burdened (HT-1080) nu/nu mice (n=3), and the effect of tumor growth was monitored over the course of two weeks, administered intravenously (for PTX-FA-HSA). Saline (n=2) was administered as a negative control. Table 4 below shows the average relative tumor volume (relative to day 0).

TABLE 4

| Day Post-Injection | PTX-FA-HSA 240 mg/kg IV (n = 3) | Saline (n = 2) |
|---|---|---|
| 0 | 1.00 | 1.00 |
| 1 | 1.05 | 0.73 |
| 3 | 1.15 | 0.81 |
| 5 | 1.58 | 2.23 |
| 7 | 3.04 | 6.17 |
| 14 | 8.68 | 22.21 |

Further, in vivo analysis of protein-bound PTX-HA in HT-1080 fibrosarcoma xenografts was carried out to measure appropriate doses and survival. Results are shown in Table 5. Doses all reported with respect to paclitaxel content of treatment. Minimum Effective Dose (MED) is defined as lowest dose necessary to extend survival beyond median survival of non-treated (saline) animals. Maximum Effective Dose (MTD) is defined as highest dose resulting in less than 10% weight loss. Therapeutic Index (TI) is defined as the ratio of MTD to MED. Median Survival is defined as the time for each cohort to drop below 50% survival. N=6 for all groups. Administration was carried out by intravenously.

TABLE 5

| Parameter | HSA-Bound PTX-FA | Saline |
|---|---|---|
| MED | 5 mg/kg | — |
| MTD | >250 mg/kg | — |
| TI | >50 | — |
| Median Survival | >70 days | 25 days |

Example 16

Particle Size by Dynamic Light Scattering

Figure 2:
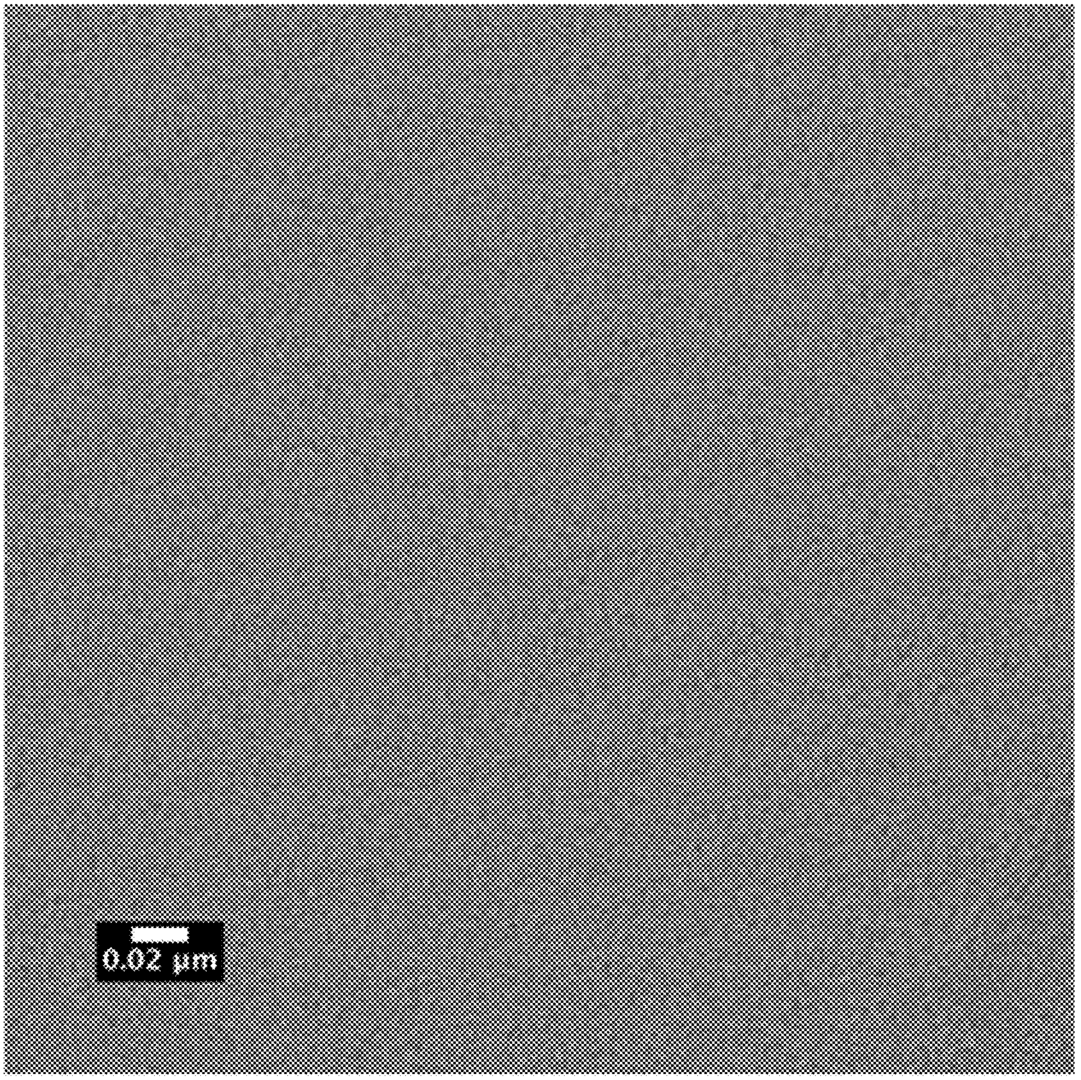
FIG. 2 shows micrograph of a cryo-TEM analysis of the PTX-FA/HSA formulation.

Multiple formulations of PTX-FA and HSA were prepared according to the method of Example 14, and varying the molar ratio of PTX-FA to HSA. For each formulation, a particle size analysis was carried out using dynamic light scattering. Table 6 shows the average radius of the particles and the percentage of particles (by mass percent) in the formulation having that respective radius. FIG. 2 shows a micrograph from a cryo-TEM (cryogenic transmission electron microscopy) at liquid nitrogen temperatures of a solution where the molar ratio of PTX-FA to HSA is 1:1. The cryo-TEM results show that the solution contains no aggregates.

TABLE 6

| Molar Ratio (PTX-FA:HSA) | Particle Radius (nm) | Percentage of Particles (mass %) |
|---|---|---|
| 1:1 | 3.4 | 99.2 |
| 2:1 | 3.5 | 96.1 |
| 3:1 | 3.6 | 95.6 |
| Free HSA | 3.5 | 99.8 |

Example 17

PTX-FA18 Binding to HSA

Using a dialysis-based protein binding assay according to the method described in Cohen, *Plasma Protein-Binding Methods in Drug Discovery* in OPTIMIZATION IN DRUG DISCOVERY: IN VITRO METHODS, Yan & Caldwell, eds., pp. 111-122 (Humana Press, Totowa, N.J., 2004), which is hereby incorporated by reference as though set forth herein in its entirety. The percentage of PTX-FA18 and the percentage of octadecanedioic acid (C18 Diacid) bound to the protein at different concentrations was measured. The results are shown in Table 7.

TABLE 7

| Concentration (μM) | % bound to protein PTXFA | % bound to protein C18 Diacid |
|---|---|---|
| 20.0 | 100.0 | 97.4 |
| 10.0 | 100.0 | 100.0 |
| 3.0 | 99.7 | 99.8 |
| 1.5 | 99.5 | 99.1 |

Example 18

In Vitro Cytotoxicity

General Cell Culture Methods:

HeLa cells were obtained from ATCC and incubated at 37° C. at 5% $CO_2$ using DMEM supplemented with 10% FBS, and lx of sodium pyruvate, non-essential amino acids, L-glutamine and antibiotics.

Cell Viability Experiments:

Cytotoxicity of compounds was evaluated using the CellTiter Blue assay (Promega). HeLa cells were plated in 96-well plates, at a density of 3000 cells/well 1 day before treatment. Treatments were prepared as 1000× serial stock dilutions in DMSO, then diluted into media for 1×, 0.1% DMSO treatment solutions. Plating media was removed, then treatments were added to the wells. After 3 days, the media was removed and replaced with 100 uL complete DMEM without phenol red. Then 20 uL of CellTiter Blue reagent was added, and the plates incubated for two hours at 37° C. Fluorescence was measured at 590 nm with excitation at 560 nm. To determine viability, average background fluorescence was subtracted from average fluorescence readings of the experimental wells (three wells per treatment concentration). Viability was calculated as the average background-subtracted signal in a well compared to that of a negative control well (treatment with 0.1% DMSO/media).

Determining $IC_{50}$:

Viabilities were fit in GraphPad Prism using a non-linear, dose-dependent inhibition curve. The ICso numbers given in the table reflect the concentration at which the cell death is 50% of the maximum response.

Results:

Table 8 shows $IC_{50}$ (measured as described above) values for various HSA/Drug-FA conjugates that were synthesized in the above examples.

TABLE 8

| Compound | $IC_{50}$ |
|---|---|
| PTX-FA18 | 64.42 nM |
| PTX-FA16 | 137.0 nM |
| PTX-FA20 | 27.8 nM |
| PTX-FAu18 | 40.06 nM |
| PTX-FAE18-Aa | 2.329 uM* |
| MTX-FA18 | 3.009 uM |
| CPT-FA18 | 10.97 uM |

Reported $IC_{50}$ values are averages of at least 3 replicates, except * which is one experiment.

The invention claimed is:

1. A compound of formula (I)

$$A^1\text{-}X^1\text{—}X^2\text{-}A^2 \qquad (I)$$

wherein:

$A^2$ is a paclitaxel moiety; and

—$X^2$—$X^1$ -$A^1$ is —C(═O)—$(CH_2)_{n1}$—C(═O)—H, wherein n1 is an integer from 12 to 24; or —$^2$—$X^1$-$A^1$ is C(═O)—$(CH_2)_7$—CH═CH—$(CH_2)_7$—C(═O)—OH.

2. The compound of claim 1 wherein the paclitaxel moiety is a moiety of the formula:

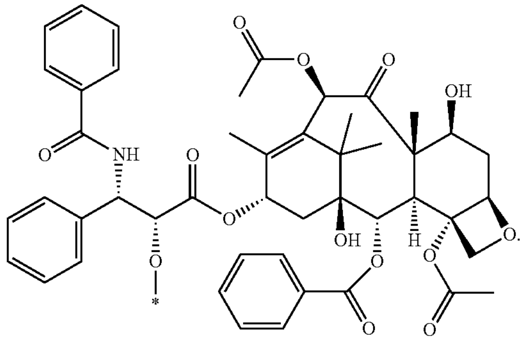 [SMILES: *O[C@@H](C(=O)O[C@H]1C[C@@]2(O)[C@@H](OC(=O)c3ccccc3)[C@@H]3[C@]4(OC(C)=O)CO[C@@H]4C[C@H](O)[C@@]3(C)C(=O)[C@H](OC(C)=O)C(=C1C)C2(C)C)[C@@H](NC(=O)c1ccccc1)c1ccccc1]

3. The compound of claim 1, which is a compound of the formula:

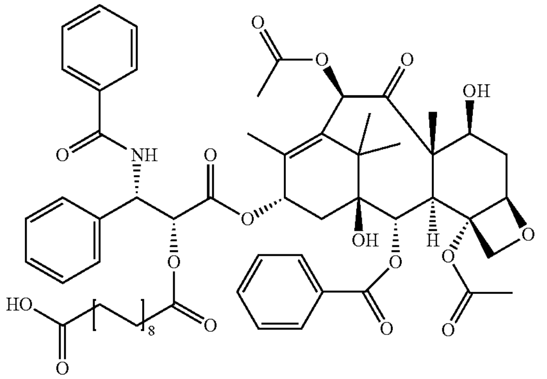

or a pharmaceutically acceptable salt thereof.

4. A pharmaceutical composition comprising:

a compound of claim 1; and a protein, wherein the protein is human serum albumin or a protein whose sequence is at least 50% equivalent to that of human serum albumin.

5. The pharmaceutical composition of claim 4, wherein the protein is human serum albumin.

6. The pharmaceutical composition of claim 4, further comprising a carrier.

7. The pharmaceutical composition of claim 6, wherein the carrier comprises water.

8. A method of treating cancer, comprising:

administering to a subject a composition of claim 4.

9. The compound of claim 2, wherein $—X^2—X^1\text{-}A^1$ is $—C(═O)—(CH_2)_{n1}—C(═O)—OH$, wherein n1is an integer from 12 to 24.

10. The compound of claim 1, wherein $—X^2—X^1\text{-}A^1$ is $—C(═O)—(CH_2)_{14}—C(═O)—OH$.

11. The compound of claim 1, wherein $—X^2—X^1\text{-}A^1$ is $—C(═O)—(CH_2)_{16}—C(═O)—OH$.

12. The compound of claim 1, wherein $—X^2—X^1\text{-}A^1$ is $—C(═O)—(CH_2)_{18}—C(═O)—OH$.

13. The compound of claim 1, wherein $—X^2—X^1\text{-}A^1$ is $—C(═O)—(CH_2)_7—CH═CH—(CH_2)_7—C(═O)—OH$.

14. The compound of claim 2, wherein $—X^2—X^1\text{-}A^1$ is $—C(═O)—(CH_2)_{14}—C(═O)—OH$.

15. The compound of claim 2, wherein $—X^2—X^1\text{-}A^1$ is $—C(═O)—(CH_2)_{18}—C(═O)—OH$.

16. The compound of claim 2, wherein $—X^2—X^1\text{-}A^1$ is $—C(═O)—(CH_2)_7—CH═CH—(CH_2)_7—C(═O)—OH$.

17. The compound of claim 1, which is a compound of the formula:

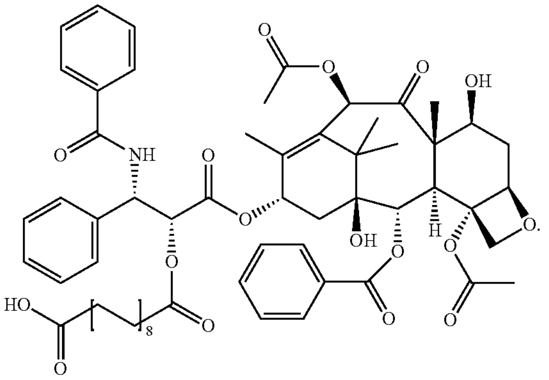

18. A pharmaceutical composition comprising:

a compound of claim 3; and a protein, wherein the protein is human serum albumin or a protein whose sequence is at least 50% equivalent to that of human serum albumin.

19. A pharmaceutical composition comprising:

a compound of claim 17; and a protein, wherein the protein is human serum albumin or a protein whose sequence is at least 50% equivalent to that of human serum albumin.

20. A method of treating cancer, comprising:

administering to a subject a composition of claim 18.

21. A method of treating cancer, comprising:

administering to a subject a composition of claim 19.

* * * * *

UNITED STATES PATENT AND TRADEMARK OFFICE

CERTIFICATE OF CORRECTION

PATENT NO. : 10,023,581 B2
APPLICATION NO. : 15/271822
DATED : July 17, 2018
INVENTOR(S) : Cassandra E. Callmann et al.

It is certified that error appears in the above-identified patent and that said Letters Patent is hereby corrected as shown below:

In Claim 1, Column 50, Line 25, delete the space between "$X^1$" and "$A^1$" and, additionally, insert an --O-- before the final "H".

In Claim 1, Column 50, Line 26, insert an --X-- between the "-" and the "$^2$".

In Claim 1, Column 50, Line 27, insert an initial -- - -- before the "C".

Signed and Sealed this
Eighteenth Day of September, 2018

Andrei Iancu
*Director of the United States Patent and Trademark Office*